United States Patent
Baker et al.

(10) Patent No.: US 11,332,768 B2
(45) Date of Patent: May 17, 2022

(54) METHODS FOR HYDROLYSING LIGNOCELLULOSIC MATERIAL

(71) Applicant: LEAF SCIENCES PTY LTD, Queensland (AU)

(72) Inventors: Alex Baker, Queensland (AU); Leslie Alan Edye, Queensland (AU)

(73) Assignee: LEAF SCIENCES PTY LTD, Queensland (AU)

( * ) Notice: Subject to any disclaimer, the term of this patent is extended or adjusted under 35 U.S.C. 154(b) by 21 days.

(21) Appl. No.: 15/324,974

(22) PCT Filed: Jul. 10, 2015

(86) PCT No.: PCT/AU2015/050390
§ 371 (c)(1),
(2) Date: Jan. 9, 2017

(87) PCT Pub. No.: WO2016/004482
PCT Pub. Date: Jan. 14, 2016

(65) Prior Publication Data
US 2017/0211108 A1    Jul. 27, 2017

(30) Foreign Application Priority Data

Jul. 10, 2014 (AU) ................................ 2014902667
Dec. 9, 2014 (AU) ................................ 2014904984

(51) Int. Cl.
*C08H 8/00* (2010.01)
*C12P 19/00* (2006.01)
(Continued)

(52) U.S. Cl.
CPC ................ *C12P 19/00* (2013.01); *C08H 6/00* (2013.01); *C08H 8/00* (2013.01); *C12P 7/10* (2013.01);
(Continued)

(58) Field of Classification Search
CPC ......... C12P 2201/00; C12P 19/00; C12P 7/10; C12P 2203/00; C08H 8/00
See application file for complete search history.

(56) References Cited

U.S. PATENT DOCUMENTS 7,455,997 B2   11/2008   Hughes
8,022,257 B2   9/2011    Li et al.
(Continued)

FOREIGN PATENT DOCUMENTS

CA        1140706      2/1983
CN        101497668 A  8/2008
(Continued)

OTHER PUBLICATIONS

European Search Report; Application No. 15818823.5; Leaf Sciences Pty Ltd.
(Continued)

*Primary Examiner* — David W Berke-Schlessel
*Assistant Examiner* — Trent R Clarke
(74) *Attorney, Agent, or Firm* — Robert C. Netter, Jr.; Dann, Dorfman, Herrell & Skillman

(57) ABSTRACT

A method for producing a partially hydrolysed lignocellulosic material is provided including treating a lignocellulosic material with an acid and/or an alkali and then a polyol. Also provided are methods of producing a fermentable sugar, or a fermentable sugar and a fermentation product from said partially hydrolysed lignocellulosic material. A partially hydrolysed lignocellulosic material, a fermentable sugar, and fermentation product produced by such methods are also provided. Also provided is an apparatus for producing a partially hydrolysed lignocellulosic material, such as by the aforementioned method.

18 Claims, 7 Drawing Sheets

(51) Int. Cl.
  *D21C 1/04* (2006.01)
  *D21C 3/02* (2006.01)
  *D21C 3/04* (2006.01)
  *D21C 1/06* (2006.01)
  *C12P 19/14* (2006.01)
  *C12P 7/6463* (2022.01)
  *C08H 7/00* (2011.01)
  *C12P 19/02* (2006.01)
  *C13K 1/02* (2006.01)
  *C12P 7/10* (2006.01)
  *C12P 7/16* (2006.01)
  *C12P 7/64* (2022.01)
  *C12M 1/00* (2006.01)

(52) U.S. Cl.
  CPC ............... *C12P 7/16* (2013.01); *C12P 7/64* (2013.01); *C12P 7/6463* (2013.01); *C12P 19/02* (2013.01); *C12P 19/14* (2013.01); *C13K 1/02* (2013.01); *D21C 1/04* (2013.01); *D21C 1/06* (2013.01); *D21C 3/02* (2013.01); *D21C 3/04* (2013.01); *C12M 45/06* (2013.01); *C12P 2201/00* (2013.01); *C12P 2203/00* (2013.01); *Y02E 50/10* (2013.01); *Y02P 20/582* (2015.11)

(56) References Cited

U.S. PATENT DOCUMENTS

| | | |
|---|---|---|
| 8,524,471 B2 | 9/2013 | Koltermann et al. |
| 8,617,851 B2 | 12/2013 | Atalla |
| 8,728,243 B2 | 5/2014 | Van Der Meulen et al. |
| 8,853,478 B2 | 10/2014 | Machhammer et al. |
| 9,447,539 B2 | 9/2016 | Zhang et al. |
| 2008/0057555 A1 | 3/2008 | Nguyen |
| 2012/0167875 A1 | 7/2012 | Qiao et al. |
| 2012/0167876 A1 | 7/2012 | Qiao et al. |
| 2012/0318258 A1 | 12/2012 | Qiao et al. |
| 2013/0164804 A1 | 6/2013 | Walther et al. |
| 2014/0093917 A1 | 4/2014 | Zhang et al. |
| 2014/0093918 A1 | 4/2014 | Zhang et al. |
| 2014/0121423 A1 | 5/2014 | Powell et al. |
| 2014/0186899 A1 | 7/2014 | Restina et al. |

FOREIGN PATENT DOCUMENTS

| | | | |
|---|---|---|---|
| CN | 101748651 B | 7/2011 | |
| CN | 103255659 A | 8/2013 | |
| EP | 0472474 A1 | 2/1992 | |
| GB | 421379 | 12/1934 | |
| GB | 576785 | 4/1946 | |
| GB | 604599 | 7/1948 | |
| GB | 2040332 A | 8/1980 | |
| WO | 2006110901 A3 | 10/2006 | |
| WO | WO-2006110891 A2 * | 10/2006 | ............... C12P 7/08 |
| WO | 2010020903 A1 | 2/2010 | |
| WO | 2010101667 A1 | 9/2010 | |
| WO | WO-2012168408 A1 * | 12/2012 | ............... C08H 8/00 |
| WO | 2013107947 A1 | 7/2013 | |
| WO | 2016004481 A1 | 1/2016 | |

OTHER PUBLICATIONS

Chen, et al., "Reducing acid in dilute acid pretreatment and the impact on enzymatic saccharification" J. Ind. Microbiol. Biotechnol. (2012) 39:691-700.

Chinese Office Action; Chinese Application No. 201580037592; Leaf Sciences Pty Ltd., Jan. 26, 2018.

* cited by examiner

MTL        RCD       560 Pressafiner       Gallons liquor =    100
O1   →    K1 | K1C    4:1, 10 min
Eucalyptus    K2         lbs acid (94% purity) =    0
chips                   Liquor flow =    20.8    USGPM
             4 g/l        (All chips & impregnated liquor go forward to digester)
             NaOH

→ I1 ──────────────────────────────→

Actual production =     69.6    ODMTPD

L:W =     1.63    at 560 Press discharge
(liquid added at 560 Press discharge)

Actual acid application =    0.00 %

Acid concentration =    0.00 g/l
Solids content (after I1 impregnation) =    0.36

560 Pressafiner            Gallons liquor =    100
4:1, 10 min
lbs acid (94% purity) =    10.9
Liquor flow =    6.5    USGPM
(All chips & impregnated liquor go forward to digester)

→ I2 ──────────────────────────→

Actual production =    57.1    ODMTPD

L:W =    0.62    at 560 Press discharge
(liquid added at 560 Press discharge)

Actual acid application =    0.76 %

Acid concentration =    12.28 g/l
Solids content (after I1 impregnation) =    0.369

FIG. 4

418 Digester            Preheat glycerol to 167 F (75 C)

Digester pressure = 75 psi           Specific Gravity of Glycerol = 1.262
Add liquor to tee piece
Glycerol flow =             0.7      USGPM
Glycerol:as is wood =   0.50
→ A1 (control water only)
→ A2 (with glycerol)
30 min retention, 5.18 bar (75 psi)

Prod'n rate =               3.7      ODMTPD

L:W =           1.71
(liquid added to digester + liquid in impregnated chips fed to digester)

Solids content (after impregnation) =        0.369

PH Profile         cook before liquor 12.91
                   K1 after liquor 11.45
                   K2 after liquor 10.90
                       Avg (K1 & K2) 11.18

I1 Pressate 5.62
   I1 Tube 5.10 (imregnator overflow pipe)
   I1 Drain 5.97 (drain liquor from impreg chips)
High water flow used for good water wash I2 before liquor (acid) 0.97                A1 filtrate 2.25
   I2 Pressate 5.68                         A2 filtrate 2.44
   I2 Drain 1.47
No tube overflow on purpose
 such that all acid gets contained in chips
going to digester

FIG. 4 cont'd

A
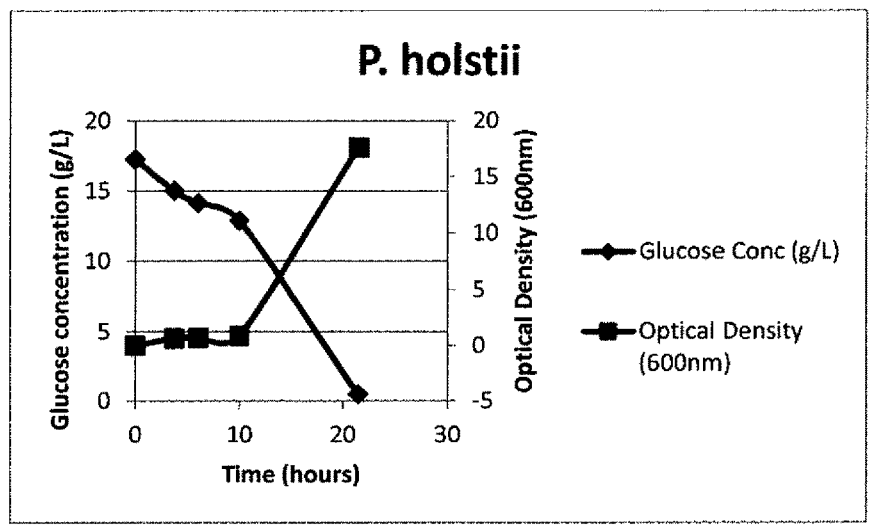
B
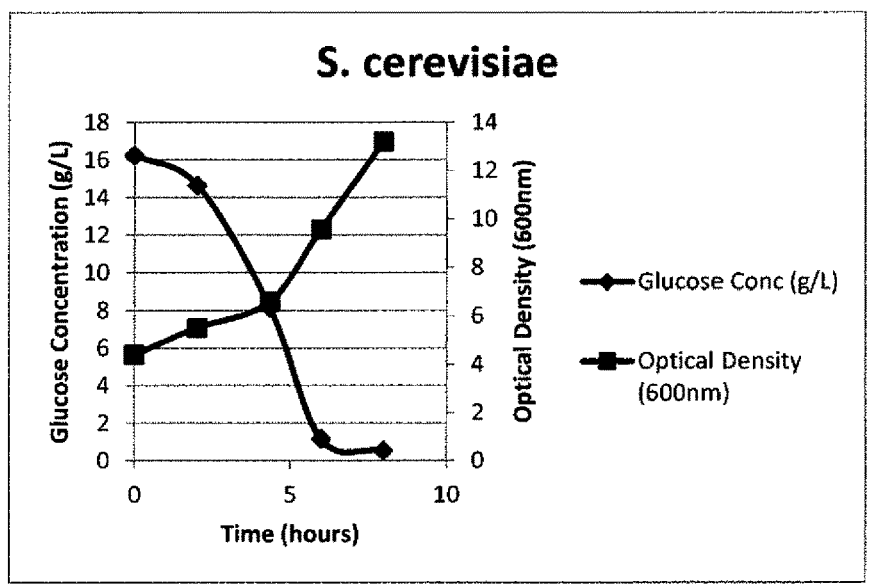
C
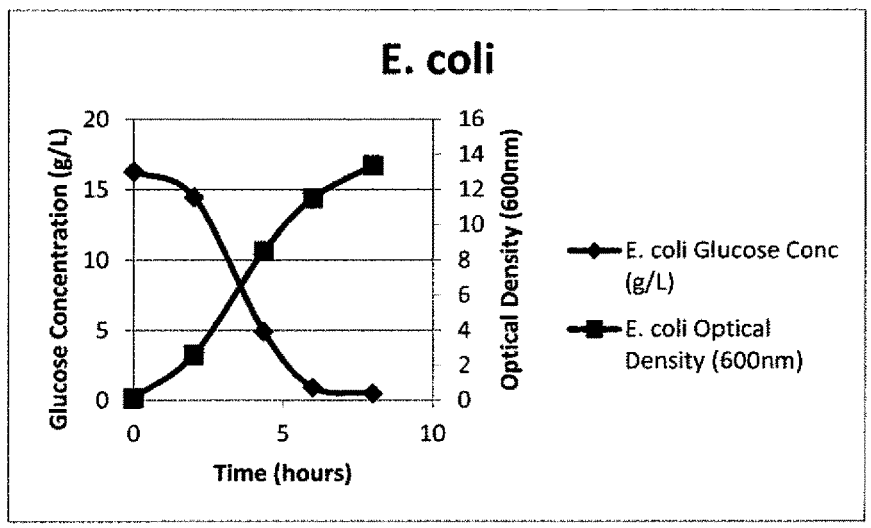
FIG. 6

METHODS FOR HYDROLYSING LIGNOCELLULOSIC MATERIAL

The present application is § 371 application of PCT/AU2015/050390 filed 10 Jul. 2015 which claims priority to 2014902667 and 2014904984 filed 10 Jul. 2014 and 9 Dec. 2014, respectively, the entire disclosures of each being incorporated by reference herein.

TECHNICAL FIELD

THIS INVENTION relates to methods for producing at least partially hydrolysed lignocellulosic material that can be subsequently used to produce useful products, such as fermentable sugars.

BACKGROUND

Lignocellulosic material can be used, amongst other things, to produce biofuels (e.g., bioethanol) and biochemicals, and thus is an alternative to fossil fuels. For efficient biofuel production from lignocellulosic materials, the cellulose and/or hemicellulose components of lignocellulosic material need to be converted to monosaccharides (i.e., monosugars) that are capable of being fermented into ethanol or butanol. Prior work in this area has proposed processes for the production of fermentable sugars from lignocellulosic material that involve a chemical and/or physical pretreatment to disrupt the natural structure of the lignocellulosic material, followed by enzymatic hydrolysis of the cellulose and hemicellulose components into monosugars. The monosugars can then be fermented to produce biofuels including ethanol or butanol, and/or other fermentation products such as organic acids and/or other alcohols. Additionally, the monosugars can be used as a carbon source for microbial conversion to other useful molecules, such as microbial lipids from, for example, *E. coli* or heterotrophic algae. However, these processes currently have not been commercialized due to the high cost, low efficiency, adverse reaction conditions, and other issues associated with the pretreatment process. In addition, these processes are not environmentally friendly and in order to achieve effective and efficient hydrolysis, a large addition of enzymes is required, which further increases costs.

Accordingly, improved methods for producing partially hydrolysed lignocellulosic material that can be used in downstream applications to produce fermentable sugars are required.

SUMMARY

The present invention is predicated in part on the surprising discovery that sequentially treating lignocellulosic material with an acid and/or an alkali, and then a polyol, and in particular glycerol, results in more efficient and improved hydrolysis or liquefaction of a lignocellulosic material compared to a single step process with a solution comprising both the acid and/or alkali and the polyol.

In a first aspect, the invention provides a method for producing an at least partially hydrolysed lignocellulosic material including the steps:
(i) treating a lignocellulosic material with an acid and/or an alkali;
(ii) treating the lignocellulosic material of step (i) with an agent that comprises, consists or consists essentially of a polyol;
thereby producing a partially hydrolysed lignocellulosic material.

In certain embodiments, at step (i) the lignocellulosic material is treated with: (a) acid alone; (b) alkali alone; (c) sequentially with acid and then alkali; or (d) sequentially with alkali and then acid.

Suitably, the acid is selected from the group consisting of sulphuric acid, hydrochloric acid, phosphoric acid, hydrofluoric acid, hydrobromic acid, nitric acid, acid metal salts and any combination thereof.

Preferably, the acid is sulphuric acid.

Suitably, the alkali is selected from the group consisting of sodium hydroxide, potassium hydroxide, ammonium hydroxide, alkali metal salts and any combination thereof.

Preferably, the alkali is sodium hydroxide.

In a preferred embodiment, step (i) includes steam impregnating the acid and/or alkali into and/or onto the lignocellulosic material.

In a preferred embodiment, the acid is present in an amount of about 0.1% to about 5% by weight of the lignocellulosic material.

In a preferred embodiment, the alkali is present in an amount of about 0.1% to about 15% by weight of the lignocellulosic material.

Suitably, the polyol is selected from the group consisting of glycerol, ethylene glycol and any combination thereof.

Preferably, the polyol is glycerol.

In one embodiment, the glycerol is or comprises crude glycerol.

Suitably, step (i) is carried out at a temperature from about 20° C. to about 99° C. or preferably from about 25° C. to about 75° C.

Suitably, step (ii) is carried out at a temperature from about 120° C. to about 200° C.

Preferably, step (ii) is carried out at a temperature of about 160° C.

Suitably, step (i) is carried out for a period of time from about 5 minutes to about 30 minutes.

Suitably, step (ii) is carried out for a period of time from about 15 minutes to about 60 minutes.

Preferably, step (ii) is carried out for a period of time of about 30 minutes.

In a particular embodiment, step (i) further comprises washing, draining and/or pressing the lignocellulosic material after treatment with the acid and/or alkali so as to, at least partly, remove the acid and/or alkali prior to the commencement of step (ii).

Suitably, the polyol is present in an amount of about 10% to about 200% by weight of the lignocellulosic material.

In a second aspect, the invention provides a partially hydrolysed lignocellulosic material produced by the method of the first aspect.

In a third aspect, the invention provides a method of producing a fermentable sugar including the step of enzymatically hydrolysing a partially hydrolysed lignocellulosic material produced according to the first aspect to produce the fermentable sugar.

Preferably, the step of enzymatically hydrolysing the partially hydrolysed lignocellulosic material is performed, at least part thereof, by contacting the partially hydrolysed lignocellulosic material with one or more enzymes selected from the group consisting of cellulases, ligninases, hemicellulases, xylanases, lipases, pectinases, amylases, proteinases, and any combination thereof.

In a fourth aspect, the invention provides a fermentable sugar produced by the method of the third aspect.

Preferably, according to the third and fourth aspects, the fermentable sugar is selected from the group consisting of glucose, xylose, arabinose, galactose, mannose, rhamnose, sucrose, fructose, and any combination thereof.

In one embodiment, the step of enzymatically hydrolysing the partially hydrolysed lignocellulosic material is carried out at a solids to liquids ratio of about 2% to about 30%.

In particular embodiments, the partially hydrolysed lignocellulosic material is contacted with a low concentration of the one or more enzymes.

In a fifth aspect, the invention provides a method of producing a fermentation product including the step of treating a fermentable sugar produced according to the third aspect to thereby produce the fermentation product.

In a sixth aspect, the invention provides a fermentation product produced by the method of the fifth aspect.

Preferably, according to the fifth and sixth aspects the fermentation product is selected from the list consisting of ethanol and butanol.

In a seventh aspect, the invention provides an apparatus for producing a partially hydrolysed lignocellulosic material comprising: a treatment chamber for treating a lignocellulosic material with an acid and/or an alkali in communication with a digestion chamber for treating the lignocellulosic material with an agent that comprises, consists or consists essentially of a polyol.

Suitably, the treatment chamber is capable of impregnating the lignocellulosic material with the acid and/or the alkali.

In certain embodiments, the apparatus further comprises a pre-treatment chamber which is capable of steaming the lignocellulosic material, such as for wetting and/or pre-heating the lignocellulosic material.

In some embodiments, the apparatus further comprises a separator for separating at least part thereof the partially hydrolysed lignocellulosic material from a liquid fraction.

In particular embodiments, the apparatus further comprises a washing device capable of washing the partially hydrolysed lignocellulosic material so as to facilitate at least partial removal of the acid, alkali and/or polyol therefrom. Preferably, the washing device is a belt vacuum filter or a walking gravity wash table adapted to facilitate continuous counter-current washing of the partially hydrolysed lignocellulosic material.

Suitably, the apparatus is suitable for use in the method of the first aspect.

Throughout this specification, unless otherwise indicated, "comprise", "comprises" and "comprising" are used inclusively rather than exclusively, so that a stated integer or group of integers may include one or more other non-stated integers or groups of integers. Conversely, the terms "consist", "consists" and "consisting" are used exclusively, such that a stated integer or group of integers are required or mandatory, and no other integers may be present. The phrase "consisting essentially of" indicates that a stated integer or group of integers are required or mandatory, but that other elements that do not interfere with or contribute to the activity or action of the stated integer or group of integers are optional.

It will also be appreciated that the indefinite articles "a" and "an" are not to be read as singular indefinite articles or as otherwise excluding more than one or more than a single subject to which the indefinite article refers. For example, "a" protein includes one protein, one or more proteins or a plurality of proteins.

BRIEF DESCRIPTION OF THE DRAWINGS

By way of example only, an embodiment of the invention is described more fully hereinafter with reference to the accompanying drawing, in which:—

FIG. 4 outlines the pretreatment method of Example 3 including alkali deacetylation prior to acid impregnation and digestion of *eucalyptus* chips.

FIG. 6 demonstrates decreases in glucose concentration and corresponding increases in cell density shown below for each for the fermentations by (A) *Pichia holstii*, (B) *Saccharomyces cerevisiae* and (C) *Escherichia coli*.

DETAILED DESCRIPTION

Figure 1:
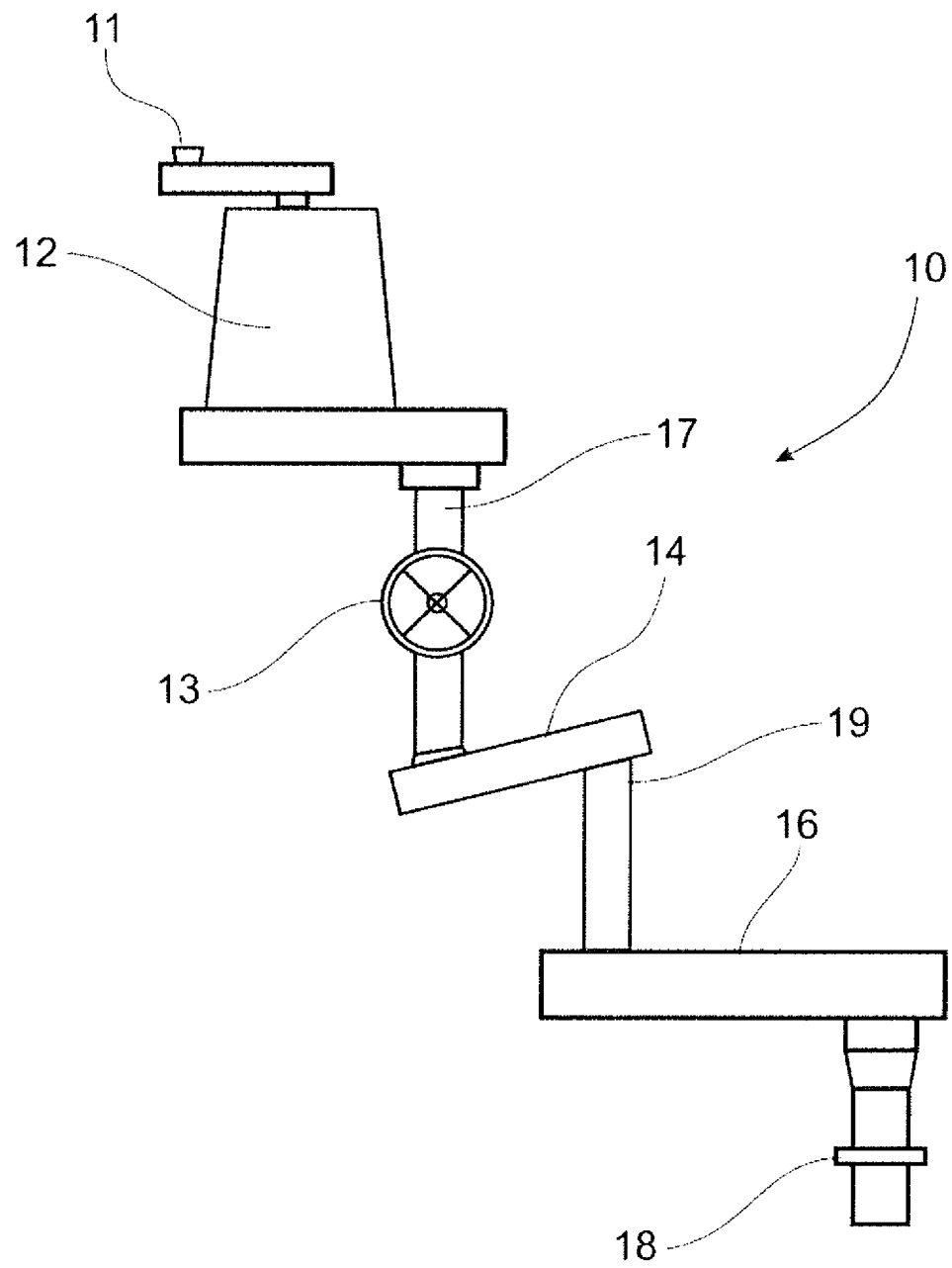
FIG. 1 is a schematic of an apparatus according to a preferred embodiment of the invention.

The present invention arises, in part, from the identification of novel methods of producing partially hydrolysed lignocellulosic material, which may be used in downstream applications to produce fermentable sugars and ultimately biochemicals. In particular these novel methods provide for an improved partially hydrolysed lignocellulosic material amenable for further liquefaction or hydrolysis. Additionally, the methods described herein typically have lower capital and operational costs and are more efficient than those previously described in the art.

The process disclosed herein provides an ability to produce more sugars quickly which is important for the economics of converting biomass to sugars, which can then be used as a base for producing green renewable bio-based products. The process disclosed herein can save significant digestion time and based on the results achieved, produce maximum sugars quicker. These results add significantly to the economic benefits of the process. Key features of the process include: a single stage continuous process; short residence time; low temperature and low pressure; low cost recyclable reagent; highly digestible carbohydrate streams; scalable and efficacious treatment demonstrated; and both non-woody and woody feedstocks. For example, the process disclosed herein can produce glucose at 99% of theoretical mass yield in 6 hours from sugar cane bagasse and 98% of theoretical mass yield in 24 hours from *Eucalyptus globulus*. Negligible degradation products such as furfural and HMF are produced.

In one aspect, the invention provides a method for producing a partially hydrolysed lignocellulosic material including the steps:

(i) treating a lignocellulosic material with an acid and/or an alkali;

(ii) treating the lignocellulosic material of step (i) with an agent that comprises, consists or consists essentially of a polyol;

thereby producing a partially hydrolysed lignocellulosic material.

The terms "lignocellulosic" or "lignocellulose", as used herein, refer to material comprising lignin and/or cellulose. Lignocellulosic material can also comprise hemicellulose, xylan, proteins, lipids, carbohydrates, such as starches and/ or sugars, or any combination thereof. Lignocellulosic material can be derived from living or previously living plant material (e.g., lignocellulosic biomass). "Biomass," as used herein, refers to any lignocellulosic material and can be used as an energy source.

Lignocellulosic material (e.g., lignocellulosic biomass) can be derived from a single material or a combination of materials and/or can be non-modified and/or modified. Lignocellulosic material can be transgenic (i.e., genetically modified). Lignocellulose is generally found, for example, in the fibers, pulp, stems, leaves, hulls, canes, husks, and/or cobs of plants or fibers, leaves, branches, bark, and/or wood of trees and/or bushes. Examples of lignocellulosic materials include, but are not limited to, agricultural biomass, e.g., farming and/or forestry material and/or residues, branches, bushes, canes, forests, grains, grasses, short rotation woody crops, herbaceous crops, and/or leaves; oil palm fibre waste such as empty fruit bunch and palm trunk; energy crops, e.g., corn, millet, and/or soybeans; energy crop residues; paper mill residues; sawmill residues; municipal paper waste; orchard prunings; Willow coppice and Mallee coppice; wood waste; wood chip, logging waste; forest thinning; short-rotation woody crops; bagasse, such as sugar cane bagasse and/or sorghum bagasse, duckweed; wheat straw; oat straw; rice straw; barley straw; rye straw; flax straw; soy hulls; rice hulls; rice straw; tobacco; corn gluten feed; oat hulls; corn kernel; fiber from kernels; corn stover; corn stalks; corn cobs; corn husks; canola; *miscanthus*; energy cane; prairie grass; gamagrass; foxtail; sugar beet pulp; citrus fruit pulp; seed hulls; lawn clippings; cotton, seaweed; trees; shrubs; wheat; wheat straw; products and/or by-products from wet or dry milling of grains; yard waste; plant and/or tree waste products; herbaceous material and/or crops; forests; fruits; flowers; needles; logs; roots; saplings; shrubs; switch grasses; vegetables; fruit peels; vines; wheat midlings; oat hulls; hard and soft woods; or any combination thereof.

For the present invention, the lignocellulosic material may have been processed by a processor selected from the group consisting of a dry grind ethanol production facility, a paper pulping facility, a tree harvesting operation, a sugar cane factory, or any combination thereof.

In some embodiments, the lignocellulosic material is bagasse.

In further embodiments, the lignocellulosic material comprises wood chip, material and/or residue preferably from *Eucalyptus globulus*, Spruce spp, African Oil palm (*Elaeis guineensis*) or any combination thereof.

By "hydrolysis" is meant the cleavage or breakage of the chemical bonds that hold the lignocellulosic material together. For instance, hydrolysis can include, but is not limited to, the breaking or cleaving of glycosidic bonds that link saccharides (i.e., sugars) together, and is also known as saccharification. Lignocellulosic material, in some embodiments, can comprise cellulose and/or hemicellulose. Cellulose is a glucan, which is a polysaccharide. Polysaccharides are polymeric compounds that are made up of repeating units of saccharides (e.g., monosaccharides or disaccharides) that are linked together by glycosidic bonds. The repeating units of saccharides can be the same (i.e., homogenous) to result in a homopolysaccharide or can be different (i.e., heterogeneous) to result in a heteropolysaccharide. Cellulose can undergo hydrolysis to form cellodextrins (i.e., shorter polysaccharide units compared to the polysaccharide units before the hydrolysis reaction) and/or glucose (i.e. a monosaccharide). Hemicellulose is a heteropolysaccharide and can include polysaccharides, including, but not limited to, xylan, glucuronoxylan, arabinoxylan, glucomannan and xyloglucan. Hemicellulose can undergo hydrolysis to form shorter polysaccharide units, and/or monosaccharides, including, but not limited to, xylose, mannose, glucose, galactose, rhamnose, arabinose, or any combination thereof.

Preferably, the method of the present invention partially hydrolyses the lignocellulosic material. "Partial hydrolysis" or "partially hydrolyses" and any grammatical variants thereof, as used herein, refer to the hydrolysis reaction cleaving or breaking less than 100% of the chemical bonds that hold the lignocellulosic material together.

In other embodiments of the present invention, the hydrolysis reaction cleaves or breaks less than 100% of the glycosidic bonds of the cellulose and/or hemicellulose present in the lignocellulosic material. In some embodiments, the partial hydrolysis reaction can convert less than about 20%, 15%, 10%, or 5% of the cellulose into glucose. In further embodiments of this invention, the partial hydrolysis reaction can convert less than about 20%, 15%, 10%, or 5% of the hemicellulose into monosaccharides. Examples of monosaccharides include but are not limited to, xylose, glucose, mannose, galactose, rhamnose, and arabinose. Additionally, the partial hydrolysis reaction may result in the recovery of greater than about 80%, 85%, 90%, or 95% of the glucan present in the partially hydrolysed lignocellulosic material compared to the amount of glucan present in the lignocellulosic material before treatment with the method described herein.

In some embodiments of the present invention, the partial hydrolysis reaction can result in the recovery of less than about 40%, 35%, 30%, 25%, 20%, 15%, 10%, or 5% of the xylan in the partially hydrolysed lignocellulosic material compared to the amount of xylan present in the lignocellulosic material before treatment with the method of the current aspect. Additionally the partial hydrolysis reaction can remove acetate from acetylated uronic acid monomers in hemicellulose present in the lignocellulosic material.

As would be readily understood by the skilled artisan, the method described herein may break down and/or remove the lignin present in the lignocellulosic material. Lignin may be removed from the lignocellulosic material by hydrolysis of the chemical bonds that hold the lignocellulosic material together. Accordingly, in some embodiments of the present invention, the method results in the removal of about 80% or less (e.g., about 80%, 75%, 70%, 65%, 60%, 55%, 50%, 45%, 40%, 35%, 30%, 25%, 20%, etc.) or any range therein of the lignin in the partially hydrolysed lignocellulosic material compared to the amount of lignin present in the lignocellulosic material prior to the treatment with the method. In some embodiments, the method results in the recovery of about 20% or more (e.g., about 20%, 25%, 30%, 35%, 40%, 45%, 50%, 55%, 60%, 65%, 70%, 75%, 80%, etc.) or any range therein of the lignin in the treated lignocellulosic material compared to the amount of lignin present in the lignocellulosic material prior to treatment with the method of the present aspect.

Furthermore, the method described herein may affect the structure of the lignocellulosic material. For instance, the method may result in the dissociation of fibers in the lignocellulosic material, increase the porosity of the lignocellulosic material, increase the specific surface area of the lignocellulosic material, or any combination thereof. In some embodiments, the method reduces the crystallinity of the cellulose structure by, for example, changing a portion of the cellulose from a crystalline state to an amorphous state.

As used herein, "treating" or "treatment" may refer to, for example, contacting, soaking, steam impregnating, spraying, suspending, immersing, saturating, dipping, wetting, rinsing, washing, submerging, and/or any variation and/or combination thereof.

Suitably, for step (i) the lignocellulosic material is treated with acid.

The skilled person would readily understand that the term "acid", as used herein, refers to various water-soluble compounds with a pH of less than 7 that can be reacted with an alkali to form a salt. Examples of acids can be monoprotic or polyprotic and can comprise one, two, three, or more acid functional groups. Examples of acids include, but are not limited to, mineral acids, Lewis acids, acidic metal salts, organic acids, solid acids, inorganic acids, or any combination thereof. Specific acids include, but are not limited to hydrochloric acid, sulfuric acid, phosphoric acid, hydrofluoric acid, hydrobromic acid, hydroiodic acid, nitric acid, formic acid, acetic acid, methanesulfonic acid, toluenesulfonic acid, boron trifluoride diethyletherate, scandium (III) trifluoromethanesulfonate, titanium (IV) isopropoxide, tin (IV) chloride, zinc (II) bromide, iron (II) chloride, iron (III) chloride, zinc (II) chloride, copper (I) chloride, copper (I) bromide, copper (II) chloride, copper (II) bromide, aluminum chloride, chromium (II) chloride, chromium (III) chloride, vanadium (III) chloride, molybdenum (III) chloride, palladium (II) chloride, platinum (II) chloride, platinum (IV) chloride, ruthenium (III) chloride, rhodium (III) chloride, zeolites, activated zeolites, or any combination thereof.

Preferably, the acid is selected from the group consisting of sulphuric acid, hydrochloric acid, phosphoric acid, hydrofluoric acid, hydrobromic acid, nitric acid, acid metal salts and any combination thereof.

Even more preferably, the acid is sulphuric acid.

Suitably, for step (i) the lignocellulosic material is treated with the alkali.

As would be readily understood by the skilled artisan, "alkali", as used herein, refers to various water-soluble compounds with a pH of greater than 7 that can be reacted with an acid to form a salt. By way of example, an alkali can include, but is not limited to, sodium hydroxide, potassium hydroxide, ammonium hydroxide, magnesium hydroxide and alkali metal salts such as, but not limited to, sodium carbonate and potassium carbonate.

Preferably, the alkali is selected from the group consisting of sodium hydroxide, potassium hydroxide, ammonium hydroxide, alkali metal salts and any combination thereof.

Even more preferably, the alkali is sodium hydroxide.

In a certain embodiment, step (i) comprises treating the lignocellulosic material sequentially with either an acid and then an alkali or an alkali and then an acid.

In a particular preferred embodiment, step (i) comprises steam impregnating the acid and/or the alkali into and/or onto the lignocellulosic material. In some embodiments, the lignocellulosic material is first pre-steamed before impregnating the acid and/or the alkali so that it is wetted and preheated by the steam. In this regard, pre-steaming typically causes cavities within the lignocellulosic material, such as the capillaries within wood chips, to become at least partly filled with liquid. The steam treatment may further cause air within the lignocellulosic material to expand and be, at least partly, expelled therefrom. Subsequently impregnating the pre-steamed lignocellulosic material may then result in the liquid within the cavities of the lignocellulosic material being replaced with the acid and/or the alkali. Alternatively, impregnation of the acid and/or the alkali may be performed without first pre-steaming the lignocellulosic material.

As would be understood by the skilled person, step (i) may simply comprise passage of the lignocellulosic material through an acid and/or alkali bath. In other embodiments, step (i) comprises passage of the lignocellulosic material through a batch vessel, wherein the batch vessel recirculates the acid and/or alkali.

In other embodiments, the lignocellulosic material may be treated with one or more acids and/or alkalis in step (i). For example, the lignocellulosic material may be treated with 1, 2, 3, 4, 5, or more acids and/or alkalis.

For step (i), the acid may be present in in an amount from about 0.1% to 5% or any range therein such as, but not limited to, about 0.3% to about 3%, or about 0.5% to about 1% by weight of the lignocellulosic material. In particular embodiments of the present invention, an acid and/or an alkali is present in step (i) in an amount of about 0.1%, 0.2%, 0.3%, 0.4%, 0.5%, 0.6%, 0.7%, 0.8%, 0.90%, 1%, 1.2%, 1.5%, 1.75%, 2%, 2.25%, 2.5%, 2.75%, 3%, 3.25%, 3.5%, 3.75%, 4%, 4.25%, 4.5%, 4.75%, 5%, or any range therein, by weight of the lignocellulosic material. In certain embodiments of the present invention, an acid and/or an alkali is present in step (i) in an amount of about 0.5% to about 2% by weight of the lignocellulosic material.

For step (i), the alkali may be present in in an amount from about 0.1% to about 15% or any range therein such as, but not limited to, about 0.3% to about 13%, or about 1% to about 10% by weight of the lignocellulosic material. In particular embodiments of the present invention, an acid and/or an alkali is present in step (i) in an amount of about 0.1%, 0.2%, 0.3%, 0.4%, 0.5%, 0.6%, 0.7%, 0.8%, 0.9%, 1%, 1.2%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15% or any range therein, by weight of the lignocellulosic material. In certain embodiments of the present invention, an alkali is present in step (i) in an amount of about 5% to about 15% by weight of the lignocellulosic material.

As would be appreciated by the skilled person, one or more steps, or part thereof, of the method of this aspect may be performed under pressure. By way of example, one or more steps of the method, or part thereof, of the present invention are performed at a pressure of about 20 psi to about 100 psi or any range therein such as, but not limited to, about 25 psi to about 75 psi, or about 40 psi to about 60 psi. In particular embodiments of the present invention, one or more steps of the method, or part thereof, are performed at a pressure of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 psi or any range therein. In one embodiment, step (i), or part thereof, is performed at a pressure of about 25 psi. In one embodiment, step (ii), or part thereof, is performed at a pressure of about 75 psi.

In particular embodiments, step (i) further comprises washing the lignocellulosic material after treatment with the acid and/or the alkali so as to, at least partly, remove the acid and/or the alkali prior to, for example, (a) a further sequential treatment with an acid or alkali; or (b) the commencement of step (ii). In one preferred embodiment, in step (i) the lignocellulosic material is treated sequentially with an alkali and then an acid, wherein step (i) further comprises washing the lignocellulosic material after treatment with the alkali and before treatment with the acid. In another preferred embodiment, in step (i) the lignocellulosic material is treated sequentially with an acid and then an alkali, wherein step (i) further comprises washing the lignocellulosic material after treatment with the acid and before treatment with the alkali.

In this regard, washing may be carried out with a wash solution and/or water. The lignocellulosic material may be washed with water and/or a wash solution one or more times, such as 2, 3, 4, or more times. Preferably, if the lignocellulosic material has been treated with an acid in step (i) it is then washed with an alkaline wash solution (i.e. pH greater than 7) and/or water thereafter. Preferably, if the lignocellulosic material has been treated with an alkali in step (i) it is then washed with an acidic wash solution (i.e. pH less than 7) and/or water thereafter. Additionally, the lignocellulosic material may be washed with water one or more times after treatment with an acid and/or an alkali in step (i), then the lignocellulosic material is washed with a alkaline or an acidic wash solution respectively one or more times, followed by optionally washing the lignocellulosic material again with water one or more times. After one or more water and/or wash solution washes, the lignocellulosic material can be separated from the water and/or wash solution via methods such as, but not limited to, vacuum filtration, membrane filtration, sieve filtration, partial or coarse separation, or any combination thereof, prior to being treated with the agent in step (ii) of the method described herein.

The term "polyol" as used herein refers to an alcohol containing multiple hydroxyl groups. Examples of polyols of the present invention include, but are not limited to, 1,2-propanediol, 1,3-propanediol, glycerol, 2,3-butanediol, 1,3-butanediol, 2-methyl-1,3-propanediol, 1,2-pentanediol, 1,3-pentanediol, 1,4-pentanediol, 1,5-pentanedial, 2,2-dimethyl-1,3-propanediol, 2-methyl-1,4-butanediol, 2-methyl-1,3-butanediol, 1,1,1-trimethylolethane, 3-methyl-1,5-pentanediol, 1,1,1-trimethylolpropane, 1,7-heptanediol, 2-ethyl-1,6-hexanediol, 1,9-nonanediol, 1,11-undecanediol, diethylene glycol, triethylene glycol, oligoethylene glycol, 2,2'-thiodiglycol, diglycols or polyglycols prepared from 1,2-propylene oxide, propylene glycol, ethylene glycol, sorbitol, dibutylene glycol, tributylene glycol, tetrabutylene glycol, dihexylene ether glycol, trihexylene ether glycol, tetrahexylene ether glycol, 1,4-cyclohexanediol, 1,3-cyclohexanediol, or any combination thereof.

Preferably, the polyol is selected from the group consisting of glycerol, ethylene glycol and any combinations thereof.

Even more preferably, the polyol is glycerol.

The polyol can be present in pure (e.g., refined or technical grade) or impure (e.g., crude or purified crude) form. In certain embodiments of the present invention, a polyol has a purity of about 70% to about 99.9% or any range therein, such as, but not limited to, about 80% to about 99.9%, or about 80% to about 97%. In particular embodiments of the present invention, the purity of a polyol is about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or any range therein. Purity forms or grades (e.g., refined, crude, or purified crude) of a polyol can be, but are not limited to, purity grades produced as by-products from biodiesel production processes. In particular embodiments of the present invention, the polyol is in pure form (e.g., having a purity of 99% or more) and in other embodiments a polyol is in crude form (e.g., having a purity of from about 70% to about 98%).

In a further embodiment, the polyol has been recovered or recycled from a lignocellulosic material-polyol mixture, such as that described herein. In this regard, the recovered or recycled polyol may be in a partially purified or refined form. To this end, the polyol may be recovered or recycled from the lignocellulose material-polyol mixture by any method or means known to those skilled in the art. Methods of recovery of the partially purified polyol may include, but are not limited to, filtration, chromatographic separation, distillation, evaporation, adsorption processes that remove contaminants, for example, percolation through columns containing activated carbon or diatomaceous earth or some other adsorptive material, and any combination thereof. Preferably, the polyol is recovered or recycled by filtration, chromatographic separation and/or evaporation.

In one embodiment, the glycerol is or comprises crude glycerol. Crude glycerol typically contains glycerol, methanol, inorganic salts, water, oils or fat, soap, and other "contaminants". Crude glycerol may be produced by a variety of natural and synthetic processes. For example, crude glycerol can be produced during the process of biodiesel production. Additionally, crude glycerol may be produced during the process of saponification (e.g., making soap or candles from oils or fats). Crude glycerol produced as a byproduct of biodiesel production typically has a glycerol content of about 40-90% and can be partially refined to remove or reduce impurities such as methanol, water, salts and soaps. Partial refinement can increase the glycerol content up to about 90% glycerol, more particularly up to about 95% glycerol and in certain cases up to about 97% glycerol, approaching the purity associated with technical grade glycerol. In particular embodiments of the present invention, the glycerol content of crude glycerol is about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97% or any range therein.

Additionally, the crude glycerol of the present invention, including the recovered or recycled glycerol described herein, may be subjected to one or more processes to render it more suitable and/or advantageous for use in the present invention without converting it to "pure" or technical grade/refined (e.g., >97% purity) glycerol. For example, crude glycerol for use in methods of the present invention may be subjected to a filtration step to remove solids and other large masses.

It would be appreciated by the skilled artisan that the glycerol to be used in the methods of the present invention may include a mixture of crude and refined (e.g., >97% purity) glycerol, including partially purified or refined glycerol, such as the recovered or recycled glycerol described herein. In accordance with certain embodiments, the amount of crude glycerol may be at least 5%, more particularly at least 25%, even more particularly at least 50%, yet even more particularly at least 75% or still yet even more particularly at least 95% by weight of a total mixture of crude and technical grade glycerol by weight. In accordance with other embodiments, the glycerol comprises substantially 100% crude glycerol.

Preferably, one or more polyols may be present in the agent. For example, 1, 2, 3, 4, 5, or more polyols can be present in the agent. A polyol can be present in the agent in an amount from about 1% to about 99% by weight of the agent or any range therein, such as, but not limited to, about 1% to about 80%, about 10% to about 50%, about 15% to about 35%, about 20% to about 99%, about 40% to about 99%, or about 80% h to about 97% by weight of the agent. In particular embodiments of the present invention, a polyol is present in the agent in an amount of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or any range therein, by weight of the agent. In particularly preferred embodiments of the present invention, the polyol is present in an amount from about 80% to about 100% by weight of the agent.

For those embodiments where the agent of step (ii) comprises less than 99.9% by weight a polyol, the agent may further comprise, for example, water, an acid or an alkali. Where the agent further comprises an acid, however, the acid is to be present in an amount no more than about 0.1% by weight of the agent. As would be appreciated by the skilled artisan, this amount of acid of no more than about 0.1% by weight of the agent would not include any residual acid remaining in and/or on the lignocellulosic material following treatment with an acid in step (i) that may subsequently mix with the agent in step (ii).

For step (ii), the agent is preferably present at an amount of about 10% to about 200% or any range therein, such as, but not limited to, about 20% to about 150%, about 30% to about 100%, or about 50% to about 70% by weight of the lignocellulosic material (i.e. the agent to lignocellulosic material ratio). In particular embodiments, the agent is present at about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200% or any range therein, by weight of the lignocellulosic material.

Suitably, step (i) is carried out at a temperature from about 20 to 99° C., or any range therein, such as, but not limited to, about 20° C. to about 90° C. or about 25° C. to about 80° C. In particular embodiments, step (i) is carried out at a temperature of about 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C. and 99° C. Preferably, step (i) is carried out at a temperature from about 25° C. to about 75° C.

Suitably, step (ii) is carried out carried out at a temperature from about 100° C. to about 220° C. or any range therein, such as, but not limited to, about 120° C. to about 200° C., about 140° C. to about 180° C., or about 150° C. to about 170° C. In particular embodiments, step (ii) is carried out at a temperature of about 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., 131° C., 132° C., 133° C., 134° C., 135° C., 136° C., 137° C., 138° C., 139° C., 140° C., 141° C., 142° C., 143° C., 144° C., 145° C., 146° C., 147° C., 148° C., 149° C., 150° C., 151° C., 152° C., 153° C., 154° C., 155° C., 156° C., 157° C., 158° C., 159° C., 160° C., 161° C., 162° C., 163° C., 164° C., 165° C., 166° C., 167° C., 168° C., 169° C., 170° C., 171° C., 172° C., 173° C., 174° C., 175° C., 176° C., 177° C., 178° C., 179° C., 180° C., 181° C., 182° C., 183° C., 184° C., 185° C., 186° C., 187° C., 188° C., 189° C., 190° C., 191° C., 192° C., 193° C., 194° C., 195° C., 196° C., 197° C., 198° C., 199° C., 200° C., 201° C., 202° C., 203° C., 204° C., 205° C., 206° C., 207° C., 208° C., 209° C., 210° C., 211° C., 212° C., 213° C., 214° C., 215° C., 216° C., 217° C., 218° C., 219° C., 220° C., or any range therein. In certain preferred embodiments, step (ii) is carried out at a temperature of about 160° C. As would be well understood by the skilled artisan, steps (i) and (ii) may be performed at different temperatures.

Step (i) is preferably performed or carried out for a period of time from about 5 minutes to about 30 minutes or any range therein, such as, but not limited to, about 5 minutes to about 25 minutes, or about 10 minutes to about 15 minutes. In certain embodiments, step (i) is carried out for a period of time of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 minutes, or any range therein. In particularly preferred embodiments, step (i) is carried out for a period of time of about 10 minutes.

Step (ii) is preferably performed or carried out for a period of time from about 5 to about 120 minutes or any range therein, such as, but not limited to, about 15 minutes to about 60 minutes, or about 20 minutes to about 40 minutes. In certain embodiments, step (ii) is carried out for a period of time of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 minutes, or any range therein. In particularly preferred embodiments, step (ii) is carried out for a period of time of about 30 minutes.

After treatment of the lignocellulosic material by the method described herein, the lignocellulosic material may be separated from a liquid fraction by any means known to those skilled in the art. Methods of separating the lignocellulosic material from the liquid fraction may include, but are not limited to, vacuum filtration, membrane filtration, sieve filtration, partial or coarse separation, or any combination thereof. The separating step can produce a liquid fraction (i.e., filtrate or hydrolysate) and a solid residue fraction (i.e., the partially hydrolysed lignocellulosic material). In some embodiments of the present invention, water and/or a wash solution is added to the treated lignocellulosic material before, during and/or after separation. A wash solution may be or comprise water, an acidic solution, an alkaline solution and/or an organic solvent, but without limitation thereto. Furthermore, in some continuous separation processes the water and/or wash solution may be added co-current or counter-current to the flow of the movement of the lignocellulosic material. For example, on a vacuum filtration belt or a gravity washing table, the wash solution may circulate through the lignocellulosic material several times flowing counter-current to the belt movement, and in this way limit the amount of wash solution needed to effectively wash the lignocellulosic material. Thus, the treated lignocellulosic material may include the agent, residual acid, residual alkali and/or by-products from the treatment process, such as, but not limited to, polyol(s), glycerol residue, and products produced from the treatment process.

Optionally, after treatment of the lignocellulosic material with the method described herein, the partially hydrolysed lignocellulosic material may be washed with a wash solution. A wash solution may comprise an acidic solution, an alkaline solution and/or an organic solvent, but without limitation thereto.

In this manner, the partially hydrolysed lignocellulosic material may be washed by any means or method known in the art. In certain embodiments, the partially hydrolysed lignocellulosic material is washed, at least partly, by a belt vacuum filter or a walking gravity wash table, such as that described herein.

In a further aspect, the invention provides a partially hydrolysed lignocellulosic material produced by the method hereinbefore described.

In yet a further aspect, the invention provides a method of producing a fermentable sugar including the step of enzymatically hydrolysing a partially hydrolysed lignocellulosic material produced according to the method hereinbefore described to produce the fermentable sugar.

As would be readily understood by the skilled person, the method hereinbefore described may make the lignocellulosic material more susceptible to enzymatic digestion or hydrolysis compared to lignocellulosic material not subjected to this method. Thus, enzymatic hydrolysis at the same enzyme dosage of the partially hydrolysed lignocellulosic material may be increased by two, three, four, five, six, seven, eight or more times compared to enzymatic digestion of lignocellulosic material not treated by the method described herein. Alternately, lower doses of enzymes can be used to obtain effective rates and yields at lower cost.

An enzyme can be microbially produced and/or plant produced, and can include, but is not limited to, a cellulase, a hemicellulase, a xylanase, a ligninase, a pectinase, a protease, an amylase, a catalase, a cutinase, a glucanase, a glucoamylase, a glucose isomerase, a lipase, a laccase, a phytase, a pullulanase, a xylose isomerase, or any combination thereof. The enzyme compositions can be prepared as a liquid, a slurry, a solid or a gel.

"Cellulase" or "cellulases", as used herein, refer to an enzyme capable of hydrolyzing cellulose to glucose. Nonlimiting examples of cellulases include mannan endo-1,4-β-mannosidase, 1,3-β-D-glucan glucanohydrolase, 1,3-β-glucan glucohydrolase, 1,3-1,4-β-D-glucan glucanohydrolase and 1,6-β-D-glucan glucanohydrolase.

"Xylanase" or "xylanases", as used herein, refer to an enzyme capable of at least hydrolyzing xylan to xylobiose and xylotriose. Examples of xylanases can be from a *Dictyoglomus* sp. including, but not limited to, *Dictyoglomus thermophilum* Rt46B.1 (See, e.g., Gibbs et al. (1995) AppL Environ. MicrobioL 61:4403-4408).

Additional nonlimiting examples of enzymes include α-L-arabinofuranosidase, α-glucuronidase, acetyl mannan esterase, acetyl xylan esterase, α-galactosidase, β-glucosidase, exoxylanase, β-1,4-xylosidase, endo-1,4-β-xylanase, endo-galactanase, endo-β-1,4-mannanase, 1,4-β-D-glucan cellobiohydrolase, endo-1,4-β-D-glucanase, β-glucosidase, endo-α-1,5-arabinanase, exo-β-1,4-mannosidase, cellobiohydrolases, endoglucanase, exo-β-1,4-xylosidase, feruloyl esterase, ferulic acid esterase, p-cumaric acid esterase, glucuronoxylan xylanohydrolase, xyloglucan endotransglycosylase, diarylpropane peroxidase, glucose oxidase, glyoxal oxidase, lignin peroxidase (LiP), manganese peroxidase, methanol oxidase, methanol oxidoreductase, phenol oxidase (laccase), phenol peroxidase, veratryl alcohol oxidase, pectolyase, pectozyme, polygalacturonase, asclepain, bromelain, caricain, chymopapain, collagenase, glycyl endopeptidase, pepsin, pronase, subtilisin, thermolysin or any combination thereof.

Additionally, enzymatic hydrolysis may involve one or more enzymes that may be a dual activity enzyme, such as an enzyme having both xylanase and cellulase activity.

Preferably, the step of enzymatically hydrolysing the partially hydrolysed lignocellulosic material is performed, at least part thereof, by contacting the partially hydrolysed lignocellulosic material with one or more enzymes selected from the group consisting of cellulases, ligninases, hemicellulases, xylanases, lipases, pectinases, amylases, proteinases, and any combination thereof.

An enzyme may be provided as a partially or fully purified full-length enzyme, or active variants or fragments thereof, or can be provided as an enzyme-producing microorganism. Moreover, any of these enzymes may be provided in an amount effective to digest or hydrolyze the partially hydrolysed lignocellulosic material, which may optionally include the acid and/or alkali, the agent and/or by-products from the method, such as, but not limited to, polyol(s), glycerol residue, and products produced from the treatment process), such as in amounts from about 0.001% to about 50%, from about 0.01% to about 50%, from about 0.1% to about 50%, from about 1% to about 50%, from about 10% to about 50%, from about 20% to about 50%, from about 30% to about 50%, from about 40% to about 50% by weight of the substrate, or more.

In one embodiment, the step of enzymatically hydrolysing the partially hydrolysed lignocellulosic material is carried out at a solids to liquids ratio of about 2% to about 30%, or any range therein, such as, but not limited to, about 3% to about 12%, or about 5% to about 10%. In certain embodiments, enzymatically hydrolysing the partially hydrolysed lignocellulosic material is carried out at a solids to liquids ratio of about 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 16.5%, 17$, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5% and 30% or any range therein. In particularly preferred embodiments, enzymatically hydrolysing the partially hydrolysed lignocellulosic material is carried out at a solids to liquids ratio of about 15%.

In particular embodiments, the partially hydrolysed lignocellulosic material is contacted with a low concentration of one or more of the one or more enzymes. By "low concentration" is meant an enzyme concentration that is lower than conventional levels typically used in saccharification, but that enzymatic hydrolysis of the partially hydrolysed lignocellulosic material still occurs or proceeds at an effective rate and yield. A skilled artisan can readily determine the suitable low concentrations for a particular enzyme. By way of example, the concentration of one or more of the one or more enzymes may be no more than 10%, preferably not more than 20%, more preferably no more than 30% or even more preferably no more than 40%, 50%, 60%, 70%, 80% or 90% of a conventional enzyme level typically used in saccharification. In particular embodiments, the concentration of one or more of the one or more enzymes is about 2 mg to about 10 mg per gram of glucan.

An enzyme composition also can include further agents known to those of skill in the art for use in processing lignocellulosic material (e.g., biomass) including, but not limited to, a chlorine, detergent, hypochlorite, hydrogen peroxide, oxalic acid, peracid, pH-regulating agent, trisodium phosphate, sodium chlorite, sodium nitrate, surfactant, urea, buffer(s), and/or water.

Examples of detergents include, but are not limited to, anionic, cationic or neutral detergents such as Nonidet (N)P-40, sodium dodecyl sulfate (SDS), sodium lauryl sulfate (SLS), sulfobetaine, n-octylglucoside, deoxycholate, Triton® X-100 (Dow Chemical Co.; Midland, Mich.) and/or Tween® 20 (ICI Americas, Inc.; Bridgewater, N.J.). Non-limiting examples of surfactants include a secondary alcohol ethoxylate, a fatty alcohol ethoxylate, a nonylphenol ethoxylate, a phosphate ester of fatty alcohols, a polyoxyethylene ether, a polyethylene glycol, a polyoxyethylenated alkyl phenol, a stearic acid and/or a tridecyl ethoxylate.

Any of the further agents can be provided as partially or fully purified. Moreover, any of these further agents can be provided in an amount from about 0.001% to about 50%, from about 0.01% to about 50%, from about 0.1% to about 50%, from about 1% to about 50%, from about 10% to about 50% h, from about 20% to about 50%, from about 30% to about 50%, from about 40% to about 50% by weight of the substrate, or more.

An enzyme composition of the present invention may also include fungi or other enzyme producing microorganisms, especially ethanologenic and/or lignin-solubilizing microorganisms, that can aid in processing, breaking down, and/or degrading lignocellulosic material. Non-limiting examples of ethanologenic and/or lignin-solubilizing microorganisms include bacteria and yeast. See generally, Burchhardt & Ingram (1992) Appl. Environ. Microbiol. 58:1128-1133; Dien et al. (1998) Enzyme Microb. Tech. 23:366-371; Keating et al. (2004) Enzyme Microb. Tech. 35:242-253; Lawford & Rousseau (1997) AppL Biochem. Biotechnol. 63-65:221-241; Handbook on Bioethanol: Production and Utilization (Wyman ed., CRC Press 1996); as well as U.S. Patent Application Publication Nos. 2009/0246841 and 2009/0286293; and U.S. Pat. No. 6,333,181. Such microorganisms may produce enzymes that assist in processing lignocellulosic material including, but not limited to, alcohol dehydrogenase, pyruvate decarboxylase, transaldolase, transketolasepyruvate decarboxylase, xylose reductase, xylitol dehydrogenase or xylose isomerase xylulokinase. In some embodiments of the invention, the ethanologenic and/or lignin-solubilizing microorganisms include, but are not limited to, members of the genera *Candida, Erwinia, Escherichia, Kebsiella, Pichia, Saccharomyces, Streptomyces* and *Zymomonas*. See, e.g., Dien (1998), supra; Ingram & Conway (1988) Appl. Environ. Microbiol 54:397-404; Jarboe et al. (2007) Adv. Biochem. Engin./Biotechnot 108:237-261; Keating et al (2004) J' Indust. Microbiol. Biotech 31:235-244; Keating et al. (2006) Biotechnol Bioeng. 93:1196-1206; Pasti et al (1990) Appl Environ. Microbiol 56:2213-2218; and Zhang et al (1995) Science 267:24010 243.

"Fermentable sugar," as used herein, refers to oligosaccharides and/or monosaccharides that may be used as a carbon source by a microorganism in a fermentation process. Examples of fermentable sugars include glucose, xylose, arabinose, galactose, mannose, rhamnose, sucrose, fructose, or any combination thereof.

In another aspect, the invention provides a fermentable sugar produced by the method described herein.

Preferably for the above aspects, the fermentable sugar is selected from the group consisting of glucose, xylose, arabinose, galactose, mannose, rhamnose, sucrose, fructose, and any combination thereof.

In yet another aspect, the invention provides a method of producing a fermentation product including the step of treating a fermentable sugar produced according to the method disclosed herein to thereby produce the fermentation product.

As would be readily understood by the skilled artisan, the fermentable sugars produced by the methods described herein may then be converted to useful value-added fermentation products, non-limiting examples of which include amino acids, such as lysine, methionine, tryptophan, threonine, and aspartic acid; vitamins; pharmaceuticals; animal feed supplements; specialty chemicals; chemical feedstocks; plastics; solvents; fuels or other organic polymers; lactic acid; butanol and/or ethanol, including fuel ethanol and/or fuel butanol, as examples of biofuels; organic acids, including acetic acid, citric acid, succinic acid and maleic acid; microbial lipids or oils, which may be used, at least in part, for biodiesel production; and/or industrial enzymes, such as proteases, cellulases, amylases, glucanases, lactases, lipases, lyases, oxidoreductases, transferases and xylanases.

Accordingly, the method of this aspect may further comprise contacting (e.g., fermenting) the partially hydrolysed lignocellulosic material, optionally including the acid, the alkali, the agent and/or by-products from the method (e.g., polyol(s), glycerol residue, and products produced from the method), with a microorganism, including, but not limited to, an ethanologenic bacteria, a yeast or a combination thereof. The contacting may occur at a pH in a range from about 2 to about 9. The partially hydrolysed lignocellulosic material may then be processed for the production of fermentable sugars and/or for biofuel (e.g., ethanol and/or butanol) production.

Additionally, the method of this aspect may further comprise contacting the partially hydrolysed lignocellulosic material, optionally including the acid, the alkali, the agent and/or by-products from the method (e.g., polyol(s), glycerol residue, and products produced from the method), with a microorganism, preferably an oleaginous microorganism, including, but not limited to, a bacteria, yeast, fungi, algae, mould or a combination thereof, to produce one or more microbial lipids.

As would be appreciated, eukaryotic yeast, mould and microalgae can synthesize lipids, such as triacylglycerols (TAGs), which are similar with the composition of vegetable oils, and prokaryotic bacteria can synthesize specific lipids.

Many oleaginous microorganisms can accumulate oils, especially TAGs, which may then be used as materials for various downstream applications, including biodiesel production.

Preferably, the fermentation product is selected from the list consisting of ethanol and butanol.

Following enzymatic hydrolysis of the partial hydrolysed lignocellulosic material, the product(s) (e.g., a fermentable sugar, ethanol, butanol, etc.) may be separated from the liquid, slurry, solid or gel. Additionally, polyol(s), alkali(s) and/or acid(s) may be collected after separation for use again (i.e., recycling of the polyol(s) and/or acid(s)) in partially hydrolysing further lignocellulosic material and/or additional treatment steps.

In another aspect, the invention provides a fermentation product produced by the method hereinbefore described.

In another aspect, the invention provides an apparatus for producing a partially hydrolysed lignocellulosic material comprising: a treatment chamber for treating a lignocellulosic material with an acid and/or an alkali in communication with a digestion chamber for treating the lignocellulosic material with an agent that comprises, consists or consists essentially of a polyol.

Suitably, the treatment chamber is capable of impregnating the lignocellulosic material with the acid and/or the alkali.

In certain embodiments, the apparatus further comprises a pre-treatment chamber which is capable of steaming the lignocellulosic material, such as for wetting and/or pre-heating the lignocellulosic material.

In some embodiments, the apparatus further comprises a separator for separating at least part thereof the partially hydrolysed lignocellulosic material from a liquid fraction.

In particular embodiments, the apparatus further comprises a washing device capable of washing the partially hydrolysed lignocellulosic material so as to facilitate at least partial removal of the acid, alkali and/or polyol therefrom. Preferably, the washing device is a belt vacuum filter or a walking gravity wash table adapted to facilitate continuous counter-current washing of the partially hydrolysed lignocellulosic material.

Suitably, the apparatus is for use in the method hereinbefore described.

A preferred embodiment of the apparatus is shown in FIG. 1. In referring to FIG. 1, the apparatus 10 comprises an inlet 11 for receiving the lignocellulosic material to be treated or digested. From the inlet 11, the lignocellulosic material enters a pre-treatment chamber 12 which is designed to apply low pressure steam to thereby pre-wet and pre-heat the lignocellulosic material. The pre-wetted and pre-heated lignocellulosic material is then transported to the treatment chamber 14 typically by gravity feed via conduit 17, wherein it is then subsequently impregnated with an acid and/or an alkali via high pressure steam. Alternatively, lignocellulosic material may enter the apparatus 10 by way of rotary valve 13, and thereby bypasses the pre-steaming/pre-wetting process of the pre-treatment chamber 12.

The apparatus 10 further comprises a digestion chamber 16 for treating or digesting lignocellulosic material with an agent comprising a polyol, and in particular glycerol. The digestion chamber 16 is designed to digest or treat acid and/or alkali treated lignocellulosic material gravity fed from treatment chamber 14 via conduit 19 under user specified temperatures and/or pressures. Preferably, the digestion chamber 16 is adapted to digest or treat the lignocellulosic material at a low liquids to solids ratio and may include rotating drums with baffles. In this regard, the digestion chamber 16 may include a number of nozzles for spraying liquid, such as glycerol, onto the lignocellulosic material. It will also be appreciated that in alternative embodiments, conduits 17 and/or 19 may comprise or be replaced by conveyors such as belt conveyors or screw augurs that facilitate movement of lignocellulosic material as described above.

As can be seen from FIG. 1, the apparatus 10 further includes a separator 18 configured to promote separation of the digested lignocellulosic material (i.e., solids fraction) from any remaining liquids fraction, such as by physically pressing the partially hydrolysed lignocellulosic material. Following passage through the separator 18, the digested lignocellulosic material may be at least partly separated from any agents, particularly liquid agents such as glycerol, added to the lignocellulosic material in the digestion chamber 16.

Although not demonstrated in FIG. 1, a conveyor is used to move the lignocellulosic material at a desired rate through and between the aforementioned chambers of the apparatus 10, including the pretreatment chamber 12, the steaming chamber 14; the digestion chamber 16; and the separator 18. Further, the conveyor may operate at a user-defined rate so as to achieve the required retention time in each chamber before moving the lignocellulosic material on to the next chamber.

Figure 2:
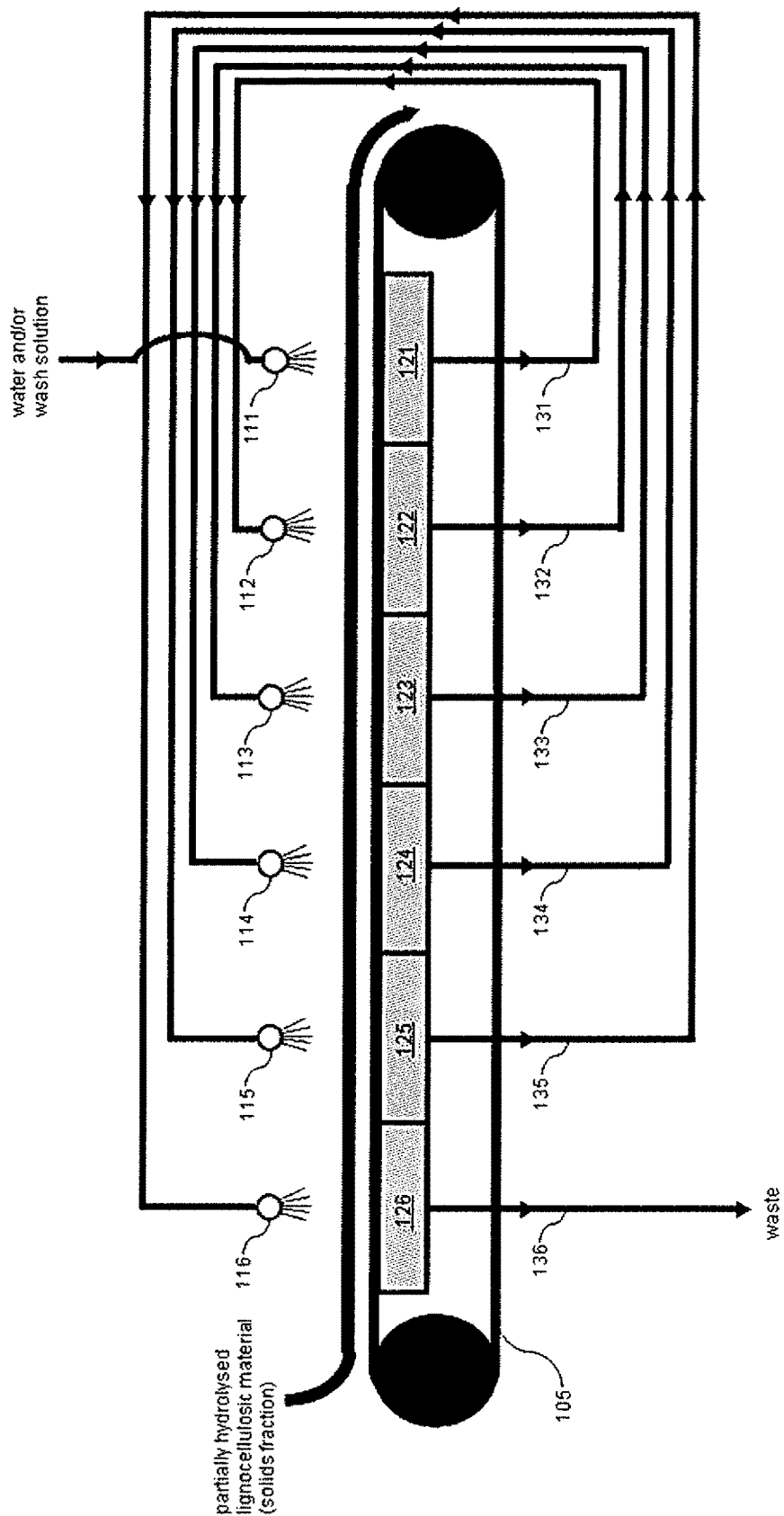
FIG. 2 is a schematic of a washing device according to a preferred embodiment of the invention.

Following separation in the separator 18, the solids fraction may be further washed by a washing device 100, an embodiment of which is provided in FIG. 2. Referring to FIG. 2, the partially hydrolysed lignocellulosic material is first fed onto a conveyor 105, which moves said material through the washing device 100 at a desired rate. Preferably, after passage through the washing device 100 the partially hydrolysed lignocellulosic material comprises a solids:liquids ratio that is suitable for downstream saccharification of said material.

As it moves through the washing device 100, the partially hydrolysed lignocellulosic material is progressively washed whilst on the conveyor 105 by way of sprayers 111, 112, 113, 114, 115, 116. Sprayers 111, 112, 113, 114, 115, 116 deliver water or wash solution onto the partially hydrolysed lignocellulosic material, after which the water or wash solution drains therefrom and collects by gravity or vacuum (vacuum pump not shown) into their respective collection trays 121, 122, 123, 124, 125, 126. As can be observed in FIG. 2, "fresh" water and/or wash solution is provided by sprayer 111 whereafter it enters at the final collection tray 121 and flows counter to the movement of the partially hydrolysed lignocellulosic material through the washing device 100.

In this regard, water and/or wash solution that has collected in the collection trays 121, 122, 123, 124, 125 is then pumped back through pipes or conduits 131, 132, 133, 134, 135 to their respective sprayers 112, 113, 114, 115, 116. In this manner, the washing device 100, allows for continuous counter-current washing of the partially hydrolysed lignocellulosic material to partially or completely remove acid, alkali, polyol and/or solutes from the lignocellulosic material with minimal water and/or wash solution use. The water and/or wash solution that has collected in collection tray 126 typically contains the highest concentration of polyol, acid, alkali, solutes etc washed from the partially hydrolysed lignocellulosic material and it is subsequently removed by pipe 136. Thus, the cleanest or freshest water and/or wash solution contacts the "cleanest" partially hydrolysed lignocellulosic material, and the more contaminated water and/or wash solution contacts the partially hydrolysed lignocellulosic material immediately as it enters the washing device 100. This method of water and/or wash solution reuse is opposed to the traditional washing method of supplying clean water and/or wash solution at every stage of the washing.

In order that the invention may be readily understood and put into practical effect, particular preferred embodiments will now be described by way of the following non-limiting examples.

Example 1

The objective of Example 1 was to evaluate methods of pretreating lignocellulosic material with a combination of glycerol and sulphuric acid that had been previously described (e.g., Zhang et al., Bioresource Technology, 2013).

Materials and Methods

Sugar cane bagasse was pretreated in a continuous horizontal digester (Andritz 418 Pressurized Horizontal Digester/Conveyor). Different glycerol: "as is bagasse" ratios and digester temperatures and pressures were evaluated. Following digestion with a solution including a combination of glycerol and sulfuric acid, the bagasse was dewatered by way of a screw press (Andritz Model 560 Pressafiner) for separation of the solid and liquid phases (hydrolysate) of the pretreated bagasse.

Briefly, the raw bagasse was first weighed and then fed into the 418 Digester System under pressure. Once within the system, there were two injection nozzles to spray glycerol and sulphuric acid at an angle onto the bagasse. Upon establishment of the desired production rate, the flow of liquor was pumped at the desired flow rate to achieve the desired glycerol to "as is" bagasse ratio. The weight of sulfuric acid added to the tank was adjusted as necessary to obtain an application of approximately 1%-1.1% on O.D. bagasse. The bagasse was then moved through the digester on a conveyer belt at the desired rate to achieve the required retention time in the digester. Following digestion, the pretreated bargasse was then transferred to the 560 Pressafiner, operating at a volumetric compression ratio of 8:1. The Pressafiner was run until all its contents were dewatered and all the hydrolysate was collected. Solids and liquid fractions from each run were collected for further analysis and subsequent enzymatic digestion (hydrolysis). The pretreated solids (washed) were tested for alpha cellulose, kappa number, % ash, carbohydrate content, acid insoluble lignin content, and enzymatic saccharification. Hydrolysate samples were tested for carbohydrate content, acid soluble lignin content, % ash, and degradation products.

Six separate pretreatment conditions in the 418 Digester System were trialed on the bagasse, and these are outlined in Table 1 below. Specifically, Table 1 provides the Glycerol: "as is bagasse" ratios, sulfuric acid applications, digester retention times and operating pressures for runs A1-A6. The digester throughputs and average fiber length are also included in Tables 1 and 3 respectively.

TABLE 1

Digester Operating Conditions and Chemical Applications

| Treatment Group | Temperature (° C.) | Solid to liquid ratio | % Sulfuric Acid on O.D. Bagasse | Retention Time (Min) | Digester Pressure (Bar) | Throughput (ODMT/D) |
|---|---|---|---|---|---|---|
| A1 | 130 | 3.3 | 1.1 | 20 | 1.7 | 3.7 |
| A2 | 160 | 2.8 | 0.92 | 20 | 5.2 | 4.4 |
| A3 | 160 | 3.1 | 1.04 | 30 | 5.2 | 3.1 |
| A4 | 130 | 4.1 | 1.05 | 30 | 1.7 | 3.2 |
| A5 | 160 | 4.2 | 1.08 | 30 | 5.2 | 3.1 |
| A6 | 160 | 2.1 | 1.04 | 30 | 5.2 | 3.2 |

Results

Upon performing the above trial a number of problems with the previously described pretreatment methods became apparent. In particular, a digester temperature of 130° C., as previously described in Zhang et al. supra, did not provide adequate fibre breakdown. A higher digester temperature of 160° C. provided improved fibre reactivity in this regard. Furthermore, relative low production rates were achieved with the bagasse owing largely to its low density. As such, material handling of the bagasse represents a significant hurdle to scaling up to commercial production.

TABLE 2

Kappa, Ash, Viscosity and Alpha Cellulose on washed pretreated solids

| Treatment Group | Kappa Number | Ash, % | Alpha Cellulose, % (mixer) | Alpha Cellulose, % (stir rod) | Chlorited Viscosity, mPa * s |
|---|---|---|---|---|---|
| Untreated Bagasse | — | 9.89 | — | — | — |
| A1 | 81.0* | 5.93 | 60.7 | NM | NM |
| A2 | 106* | 7.65 | 71.1 | 74.1 | 13.7 |
| A3 | 118* | 7.36 | 74.7 | 77.8 | 13.1 |
| A4 | 81.0* | 6.27 | 62.1 | 62.3 | 16.0 |
| A5 | 112* | 7.28 | 73.5 | 77.4 | 17.0 |
| A6 | 124* | 8.94 | 77.4 | 77.9 | 12.7 |

TABLE 3

Carbohydrate composition of the washed pretreated solids fraction

| Treatment Group | Average Fiber Length (mm) | Arabinan (%) | Galactan (%) | Glucan (%) | Xylan (%) | Mannan (%) | Hemis (%) | Total Carbs (%) | Hemi/Total | Acid Soluble Lignin (%) | Acid Insoluble Lignin (%) | Acid Insoluble Residue (%) |
|---|---|---|---|---|---|---|---|---|---|---|---|---|
| Untreated Bagasse | ND | 01.9 | 0.6 | 41.1 | 22.1 | 0.8 | 25.3 | 66.3 | 0.38 | 3.8 | 18.9 | 6.4 |
| A1 | 0.48 | 1.2 | 0.4 | 43.0 | 20.1 | 0.6 | 22.4 | 65.4 | 0.34 | 3.9 | 19.8 | 4.0 |
| A2 | 0.47 | 0.8 | 0.3 | 48.5 | 15.9 | 0.6 | 17.6 | 66.2 | 0.27 | 3.4 | 19.5 | 5.8 |
| A3 | 0.50 | 0.7 | 0.3 | 50.0 | 15.2 | 0.6 | 16.8 | 66.9 | 0.25 | 3.1 | 19.5 | 5.5 |
| A4 | 0.45 | 1.0 | 0.4 | 44.8 | 20.8 | 0.6 | 22.8 | 67.6 | 0.34 | 3.4 | 19.5 | 4.5 |

TABLE 3-continued

Carbohydrate composition of the washed pretreated solids fraction

| Treatment Group | Average Fiber Length (mm) | Arabinan (%) | Galactan (%) | Glucan (%) | Xylan (%) | Mannan (%) | Hemis (%) | Total Carbs (%) | Hemi/Total | Acid Soluble Lignin (%) | Acid Insoluble Lignin (%) | Acid Insoluble Residue (%) |
|---|---|---|---|---|---|---|---|---|---|---|---|---|
| A5 | 0.52 | 0.7 | 0.3 | 49.6 | 15.1 | 0.6 | 16.7 | 66.2 | 0.25 | 3.3 | 19.0 | 6.0 |
| A6 | 0.49 | 0.6 | 0.3 | 49.3 | 11.9 | 0.6 | 13.4 | 62.7 | 0.21 | 3.6 | 20.3 | 7.2 |

TABLE 4

Carbohydrate composition of the washed pretreated liquids fraction

| Treatment Group | Arabinose (mg/L) | Galactose (mg/L) | Glucose (mg/L) | Xylose (mg/L) | Mannose (mg/L) | Hemis (mg/L) | Total Carbs (mg/L) | Hemi/Total | Acid Soluble Lignin (%) |
|---|---|---|---|---|---|---|---|---|---|
| A1 | 412 | 147 | 576 | 1112 | ND | 1670 | 2246 | 0.74 | 0.2 |
| A2 | 786 | 217 | 973 | 4951 | 148 | 6103 | 7075 | 0.86 | 0.4 |
| A3 | 688 | 267 | 915 | 4800 | 201 | 5956 | 6871 | 0.87 | 0.4 |
| A4 | 309 | 120 | 382 | 954 | 117 | 1501 | 1883 | 0.80 | 0.3 |
| A5 | 590 | 207 | 702 | 3859 | 134 | 4790 | 5492 | 0.87 | 0.4 |
| A6 | 1110 | 367 | 1404 | 8200 | 199 | 9875 | 11279 | 0.88 | 0.5 |

TABLE 5

Enzymatic Hydrolysis of Glucan to Glucose by Ctec 3 cellulases (HPLC)

| Glucose (ppm) conversions | 0 hr | 6 hr | 24 hr | 52 hr | 72 hr | 168 hr | SAC pH | Yield (%) | Yield$_{168}$ (%) | STDe | Yield$_{72}$ (%) | Yield$_{72}$ (%) | STDe |
|---|---|---|---|---|---|---|---|---|---|---|---|---|---|
| blank | 374 | 407 | 356 | 417 | 433 | 374 | 5.01 | #DIV/0! | | | #DIV/0! | | |
| SRP | 1414 | 13556 | 19246 | 18943 | 16510 | 18998 | 4.93 | 83.82% | 83.82% | 0.00% | 72.35% | 72.35% | 0.00% |
| SRP | 5% | 59.18% | 85.01% | 85.38% | 72.35% | 83.82% | | | | | | | |
| A1: 3.3 Gly; 1.1 H2SO4 | 1306 | 6018 | 6140 | 7695 | 7936 | 8549 | 4.85 | 36.81% | 36.82% | 0.02% | 33.78% | 33.79% | 0.02% |
| A1: 3.3 Gly; 1.1 H2SO4 | | | | 7687 | 7941 | 8556 | 4.84 | 36.84% | | | 33.80% | | |
| | 4% | 25.26% | 26.04% | 32.75% | 33.79% | 36.82% | | | | | | | |
| A2: 2.8 Gly; 0.92% H2SO4 | 1530 | 12536 | 15468 | 15333 | 15576 | 16438 | 4.78 | 72.27% | 73.04% | 1.09% | 68.13% | 68.70% | 0.81% |
| A2: 2.8 Gly; 0.92% H2SO4 | | | | 15553 | 15830 | 16781 | 4.79 | 73.81% | | | 69.27% | | |
| | 5% | 54.57% | 67.99% | 67.60% | 68.70% | 7304% | | | | | | | |
| A3: 3.1 Gly; 1.04 H$_2$SO$_4$ | 1282 | 12954 | 15480 | 16017 | 16178 | 17128 | 4.78 | 75.42% | 75.08% | 0.49% | 70.88% | 68.45% | 3.43% |
| A3: 3.1% Gly; 1.04 H$_2$SO$_4$ | | | | 15994 | 15099 | 16975 | 4.80 | 74.73% | | | 66.02% | | |
| | 4% | 56.48% | 68.08% | 70.17% | 68.45% | 75.08% | | | | | | | |
| A4: 4.1 Gly; 1.05% H2SO4 | 1456 | 6214 | 7004 | 8503 | 8506 | 9578 | 4.82 | 41.43% | 40.70% | 1.03% | 36.34% | 36.12% | 0.31% |
| A4: 4.1 Gly; 1.055 H2SO4 | | | | 8236 | 8408 | 9255 | 4.82 | 39.97% | | | 35.90% | | |
| | 5% | 26.14% | 29.92% | 35.79% | 36.12% | 40.70% | | | | | | | |
| A5: 4.2 Gly 1.08% H2SO4 | 1651 | 12355 | 15226 | 16119 | 16372 | 16894 | 5.00 | 7433% | 74.52% | 0.27% | 71.71% | 71.47% | 0.34% |
| A5: 4.2% Gly 1.08% H2SO4 | | | | 15159 | 16265 | 16980 | 4.80 | 74.71% | | | 71.23% | | |
| | 6% | 53.75% | 66.90% | 68.48% | 71.47% | 74.52% | | | | | | | |
| A6: 2.1 Gly; 1.04% H2SO4 | 1909 | 14624 | 17172 | 18156 | 18483 | 18981 | 4.91 | 83.77% | 84.45% | 0.97% | 81.26% | 81.71% | 0.64% |
| A6: 2.1% Gly; 1.04% H2SO4 | | | | 17044 | 18684 | 19286 | 4.88 | 85.14% | | | 82.17% | | |
| A6: 2.1% Gly; 1.04% H2SO4 | 7% | 64.00% | 75.70% | 77.36% | 81.71% | 84.454% | | | | | | | |

TABLE 6

Enzymatic Hydrolysis of Xylan to Xylose by Ctec 3 cellulases (HPLC)

| Xylose (ppm) conversions | 0 hr | 6 hr | 24 hr | 52 hr | 72 hr | 168 hr | Yield (%) | Yield avg | STDev |
|---|---|---|---|---|---|---|---|---|---|
| blank | 252 | 298 | 294 | 272 | 316 | 229 | 0.00 | | |
| SRP Control | 418 | 1668 | 2599 | 2950 | 3107 | 3656 | 131% | 130.84% | |

TABLE 6-continued

Enzymatic Hydrolysis of Xylan to Xylose by Ctec 3 cellulases (HPLC)

| Xylose (ppm) conversions | 0 hr | 6 hr | 24 hr | 52 hr | 72 hr | 168 hr | Yield (%) | Yield avg | STDev |
|---|---|---|---|---|---|---|---|---|---|
| SRP Control | | 6% | 52% | 88% | 102% | 107% | 131% | | |
| | 472 | 1901 | 2132 | 2565 | 2794 | 2950 | 23% | 23% | 0% |
| A1: 3.3 Gly; 1.1 H2SO4 | 472 | | | 2612 | 2839 | 2992 | 24% | | |
| A1: 3.3 Gly; 1.1 H2SO4 | 0.00% | 13.43% | 15.60% | 19.89% | 22.04% | 23.49% | | | |
| | 543 | 2896 | 3740 | 3783 | 4038 | 4291 | 50% | 51% | 0% |
| A2: 2.8 Gly; 0.92% H2SO4 | 543 | | | 3809 | 4080 | 4337 | 51% | | |
| A2: 2.8 Gly; 0.92% H2SO4 | 0.00% | 31.58% | 42.91% | 43.66% | 47.19% | 50.61% | | | |
| | 492 | 3020 | 3847 | 3962 | 4259 | 4382 | 56% | 56% | 1% |
| A3: 3.1 Gly; 1.04 H$_2$SO4 | 492 | | | 3920 | 3949 | 4323 | 55% | | |
| A3: 3.1% Gly; 1.04 H2SO4 | 0.00% | 36.56% | 48.52% | 49.88% | 52.23% | 55.83% | | | |
| | 489 | 219 | 2452 | 2949 | 3140 | 3489 | 28% | 29% | 0% |
| A4: 4.1 Gly; 1.05% H2SO4 | 489 | | | 3024 | 3304 | 3559 | 29% | | |
| A4: 4.1% Gly; 1.05% H2SO4 | 0.00% | 15.45% | 18.60% | 23.67% | 25.90% | 28.77% | | | |
| | 676 | 3225 | 4196 | 4385 | 4697 | 4945 | 62% | 60% | 2% |
| A5: 4.2 Gly; 1.08% H2SO4 | 676 | | | 4146 | 4693 | 4770 | 59% | | |
| A5: 4.2% Gly; 1.08% H2SO4 | 0.00% | 36.84% | 50.88% | 51.88% | 58.09% | 60.44% | | | |
| | 521 | 3049 | 3758 | 3966 | 4298 | 4422 | 72% | 72% | 0% |
| A6: 2.1 Gly; 1.04% H2SO4 | 521 | | | 3767 | 4371 | 4445 | 72% | | |
| A6: 2.1% Gly; 1.04% H2SO4 | 0.00% | 46.49% | 59.53% | 61.53% | 70.14% | 71.96% | | | |

Example 2

The objective of this trial was to evaluate different glycerol and sulfuric acid treatments applied to three different substrates, bagasse, white spruce wood chips, and *Eucalyptus globulus* wood chips, in an attempt to improve on those pretreatment methods for lignocellulosic material previously described.

Materials and Methods

For the trial runs involving bagasse, the bagasse was fed directly into a 418 horizontal pressurized digester using a plug screw feeder, wherein both glycerol and sulfuric acid were added at the inlet to the digester. This process was similar to that described for Example 1. In this trial, steam impregnation was not performed on the bagasse. Later trials, however, demonstrated effective pre-digester impregnation of bagasse with acid.

For the trial runs involving spruce and *eucalyptus* wood chips, the wood chips were initially compressed, de-structured, and impregnated with either water or sulfuric acid in an Andritz 560 GS Impressafiner prior to being fed into a 418 horizontal pressurized digester. Glycerol with or without sulphuric acid was then added to the impregnated wood chips at the inlet to the digester. The initial chip destructing and impregnation were performed on the wood substrates in an attempt to better penetrate their fibrous structure during the pretreatment process.

Table 7 below provides the reaction parameters for each of the pretreatment trials of the bagasse, spruce and *eucalyptus* materials. The reaction time in the 418 digester for all runs was 30 minutes.

TABLE 7

Digester Operating Conditions and Chemical Applications

| Run No. | Material | Impregnation | H$_2$SO$_4$ added at digester | Glycerol: As Is Substrate | % Sulfuric Acid on O.D. Wood | Liquor Flow to 418 Digester (gpm) | Digester temperature (° C.) | Digester Pressure (bar) |
|---|---|---|---|---|---|---|---|---|
| A1 | Bagasse | No | Yes | 3.0 | 2.3 | 2.4 | 130 | 1.7 |
| A2 | Bagasse | No | Yes | 3.0 | 2.3 | 2.4 | 160 | 5.2 |
| A3 | Bagasse | No | Yes | 2.0 | 1.5 | 1.6 | 160 | 5.2 |
| A4 | Bagasse | No | Yes | 1.0 | 1.4 | 0.8 | 160 | 5.2 |
| A5 | Spruce | Yes (water) | Yes | 0.6 | 1.5 | 1.0 | 160 | 5.2 |
| A6 | Spruce | Yes (H$_2$SO$_4$) | No | 0.6 | 1.5 | 1.0 | 160 | 5.2 |
| A7 | Spruce | Yes (H$_2$SO$_4$) | No | 0.6 | 1.0 | 1.0 | 160 | 5.2 |
| A8 | *Eucalyptus* | Yes (H$_2$SO$_4$) | No | 1.0 | 1.0 | 1.0 | 160 | 5.2 |
| A9 | *Eucalyptus* | Yes (H$_2$SO$_4$) | No | 1.0 | 0.5 | 1.0 | 160 | 5.2 |
| A10 | *Eucalyptus* | Yes (H$_2$SO$_4$) | No | 0.5 | 0.5 | 0.5 | 160 | 5.2 |
| A11 | *Eucalyptus* | Yes (H$_2$SO$_4$) | No | 0.0 | 0.5 | 1.0 | 160 | 5.2 |

Digestion in the 418 Digester was performed similarly to that described for Example 1 except that Runs A6 to A11 received no further sulphuric acid therein. Following digestion, the pretreated samples from particular runs (A1-A5, A8-A11) were then transferred to the 560 Pressafiner, such that the solids and liquid fractions could collected for further analysis and subsequent enzymatic digestion (hydrolysis). The pretreated solids (washed) were tested for alpha cellulose, kappa number, % ash (Table 10), carbohydrate content, acid insoluble lignin content (Tables 11), and enzymatic saccharification (Tables 13). Hydrolysate samples were tested for carbohydrate content and acid soluble lignin content (Table 12). All pulps were further tested to standard Tappi procedures including Canadian Standard Freeness, L&W Fibre Test, bulk density and solids content.

For enzymatic saccharification, the same experimental conditions were applied as described in the NREL Enzymatic Saccharification of Lignocellulosic Biomass Laboratory Analytical Procedure (M. Selig, N. Weiss, and Y. Ji, NREL/TP-510-42629 March 2008). The procedure measures the efficacy of a given pretreatment based on a maximum enzyme loading and is reported as a percentage of the theoretical mass yield. Cellulase enzyme cocktail used was Cellic® CTec3 (Cellic® CTec3 is a registered trademark of Novozymes) at 20 FPU/g cellulose at 2% cellulose weight loading applied to initial samples reported in Table 13.

Material generated as samples A2 (bagasse pretreated biomass) & A8 (Eucalypt pretreated biomass) were further evaluated to observe the effect of increasing biomass solids loading on enzymatic hydrolysis. A pH of 5.0 and a temperature of 50° C. were the optimal reaction conditions. A 20 mg/g glucan enzyme dose was tested.

Results

From the above trials on the three lignocellulosic substrates, the degree of digestion or reaction was largely influenced by the percentage of sulphuric acid added. Accordingly, the amount of glycerol relative to the lignocellulosic substrate could be significantly reduced without any apparent impact on the digested material as per a visual assessment. Accordingly, pretreatment reactions were successfully performed at extremely low liquids to solids ratios, such that there is little or no free liquid within the digester. For example, the *eucalyptus* wood chip reacted extremely well at acid 0.7% on chip and 0.3 kg/kg Glycerol/chip which represents a liquids to solids ratio for the digestion of only 0.24:1.

For the bagasse, 130° C. at 2.4% acid still did not react the fibre fully as compared with bagasse digested at 160° C., reinforcing what was seen in Example 1. Digesting bagasse at 160° C. and 2.4% acid resulted in mud-like material that could not be pressed, indicating that the substrate was totally reacted. By decreasing the acid in the digester some fibre was retained, but the digested bagasse was more readily pressed.

Interestingly, for the spruce trial run (A6: 1.5% acid, 0.6 glycerol ratio) where the chips were impregnated with sulphuric acid by the Impressfiner, a lower freeness was observed than for the spruce trial run (A7: 1.5% acid, 0.6 glycerol ratio) where the sulphuric acid was added at the digester (Table 9). This suggests that the wood chips impregnated with acid prior to digestion and treatment with glycerol were better reacted than those not impregnated with acid, but digested with a solution of combined acid and glycerol. As such, the impregnation of lignocellulosic material with sulphuric acid prior to the addition of glycerol at the digestion step was superior to adding acid at the same time as glycerol to the digester.

The *eucalyptus* trial runs suggest that significant reductions in glycerol application are possible without affecting digestion of the lignocellulosic substrate. Eliminating glycerol altogether from the pretreatment reaction (A11: 0.5% acid), however, demonstrated the highest freeness thereby indicating a lower digestion reactivity. The *eucalyptus* run (A10: 0.5% acid, 0.3 glycerol ratio) performed at a similar acid concentration, but with glycerol, had a significantly lower freeness (159 mL versus 467 mL) indicating a higher reactivity. Furthermore, enzymatic digestion of A10 material compared with the A11 material supports the effect of glycerol in the process sequence, demonstrated by a 7.08% difference in glucose yield at 72 hrs (A10=94.82% STDe 0.46%; A11=87.74% STDe 0.80%)

With regards to the effect of increasing biomass solids on enzymatic hydrolysis, an increase in solids loading from 2% to 10% did not adversely affect the digestion rate and % conversion of glucan to glucose (Table 15). This is an important aspect with respect to industrial application of the resultant biomass and its conversion to fermentable sugars.

TABLE 8

Material characteristics

| Lignocellulosic Material | % O.D. Solids (%) | Bulk density - wet (kg/m$^3$) | Bulk density - dry (kg/m$^3$) |
|---|---|---|---|
| Soaked spruce | 70.0 | 179.42 | 125.60 |
| Eucalyptus | 81.8 | 224.28 | 183.46 |
| Soaked *Eucalyptus* | 58.8 | 320.40 | 188.40 |
| Bagasse | 57.5 | 86.51 | 49.74 |

TABLE 9

Reaction Summary

| Run No. | Material | Freeness (CSF) | Refining Energy (kWh/ODMT) | Average Fibre Length (mm) |
|---|---|---|---|---|
| A1 | Bagasse | 325 | 38 | 0.51 |
| A2 | Bagasse | 69 | 68 | 0.44 |
| A3 | Bagasse | 92 | 60 | 0.46 |
| A4 | Bagasse | 149 | 51 | 0.46 |
| A5 | Spruce | 457 | 31 | 0.45 |
| A6 | Spruce | 294 | 17 | 0.33 |
| A7 | Spruce | 195 | 18 | 0.36 |
| A8 | *Eucalyptus* | 132 | 12 | 0.42 |
| A9 | *Eucalyptus* | 189 | 11 | 0.42 |
| A10 | *Eucalyptus* | 159 | 18 | 0.40 |
| A11 | *Eucalyptus* | 467 | 17 | 0.44 |

TABLE 10

Kappa, Ash, Viscosity and Alpha Cellulose on washed pretreated solids

| Sample Description | Kappa Number, As is | Kappa Number, ground | Ash, % | Alpha Cellulose, % (mixer) | Chlorited Viscosity, mPa * s |
|---|---|---|---|---|---|
| *Eucalyptus* Soak | NR | NR | 0.41 | NR | NR |
| Spruce | NR | NR | 0.12 | NR | NR |
| A1 Washed | 122.0 | 141.0 | 9.75 | 70.4 | 11.4 |
| A2 Washed | 133.8 | 108.2 | 13.7 | 77.7 | 4.35 |
| A4 Washed | 164.0 | 148.1 | 11.1 | 71.0 | 8.33 |
| A7 Washed | 117.3 | 170.1 | 0.04 | 24.0 | 3.89 |
| A8 Washed | 146.5 | 171.4 | 0.09 | 74.7 | 7.02 |
| A9 Washed | 148.1 | 163.3 | 0.07 | 72.3 | 10.8 |
| A10 Washed | 146.1 | 164.2 | 0.08 | 75.3 | 9.37 |
| A11 Washed | 109.1 | 151.4 | 0.13 | 70.4 | 14.2 |

TABLE 11

Solid Carbohydrates

| Descriptive ID | Arabinan (%) | Galactan (%) | Glucan (%) | Xylan (%) | Mannan (%) | Hemis (%) | Total Carbs (%) | Hemi/Total | Acid Soluble Lignin (%) | Acid Insoluble Lignin (%) | Acid Insoluble Residue (%) |
|---|---|---|---|---|---|---|---|---|---|---|---|
| *Eucalyptus* Soak | 0.3 | 1.3 | 44.1 | 14.0 | 1.0 | 16.5 | 60.7 | 0.27 | 4.4 | 22.2 | 0.0 |
| Spruce | 1.1 | 2.3 | 43.8 | 5.3 | 12.3 | 21.0 | 64.8 | 0.32 | 0.4 | 29.5 | 0.0 |
| A1 | 0.5 | 0.2 | 46.3 | 12.3 | 0.2 | 13.2 | 59.5 | 0.22 | 1.5 | 21.6 | 7.5 |
| A2 Washed | 0.2 | <0.1 | 52.1 | 4.3 | 0.1 | 4.7 | 56.8 | 0.08 | 1.1 | 21.4 | 10.4 |
| A4 | 0.5 | <0.1 | 46.2 | 10.1 | 0.1 | 10.8 | 57.1 | 0.19 | 1.4 | 24.7 | 8.4 |
| A7 Washed | <0.1 | 0.2 | 52.8 | 1.3 | 1.2 | 2.7 | 55.5 | 0.05 | 0.3 | 40.2 | 0.0 |
| A8 Washed | <0.1 | <0.1 | 60.5 | 2.7 | 0.4 | 3.2 | 63.7 | 0.05 | 1.9 | 29.8 | 0.0 |
| A9 Washed | <0.1 | 0.1 | 56.5 | 3.6 | 0.6 | 4.3 | 60.8 | 0.07 | 2.2 | 28.1 | 0.1 |
| A10 | <0.1 | 0.1 | 60.2 | 3.3 | 0.4 | 4.0 | 64.1 | 0.06 | 2.3 | 28.8 | 0.0 |
| A11 Washed | <0.1 | 0.2 | 55.3 | 4.8 | 0.6 | 5.7 | 61.0 | 0.09 | 2.6 | 27.5 | 0.0 |

TABLE 12

Liquid Carbohydrates

| Descriptive ID | Arabinose (mg/L) | Galactose (mg/L) | Glucose (mg/L) | Xylose (mg/L) | Mannose (mg/L) | Hemis (mg/L) | Total Carbs (mg/L) | Hemi/Total | Acid Soluble Lignin (%) |
|---|---|---|---|---|---|---|---|---|---|
| A1 Pressate | 1665 | 633 | 4645 | 14781 | 300 | 17379 | 22023 | 0.79 | 0.4 |
| A2 Filtrate | 809 | 275 | 1663 | 7761 | 132 | 8977 | 10640 | 0.84 | 0.4 |
| 2196-2 P4 Pressate | 2427 | 4491 | 5112 | 8200 | 14170 | 29288 | 34400 | 0.85 | 0.3 |
| A5 Pressate | 200 | 830 | 489 | 8898 | 440 | 10368 | 10857 | 0.95 | 0.1 |
| A11 Pressate | 935 | 3994 | 2974 | 41863 | 2159 | 48950 | 51924 | 0.94 | 0.4 |

TABLE 13

Enzymatic Hydrolysis of Glucan to Glucose by Ctec 3 cellulases (HPLC)

| Glucose (ppm) conversions | 0 | 6 | 24 | 52 | 72 | 168 | SAC pH | Yield (%) | Yield$_{168}$ (%) | STDe | Yield$_{72}$ (%) | Yield$_{72}$ (%) | STDe |
|---|---|---|---|---|---|---|---|---|---|---|---|---|---|
| blank | 270 | 328 | 292 | 241 | 258 | 295 | 4.93 | #DIV/0! | | | #DIV/0! | | |
| SRP | 1568 | 14249 | 19874 | 21127 | 20597 | 20213 | 2.89 | 89.64% | 89.64% | 0.00% | 91.53% | 91.53% | 0.00% |
| SRP | 6% | 63.06% | 88.13% | 94.00% | 91.53% | 89.64% | | | | | | | |
| A2 | 3851 | 22342 | 23707 | 23130 | 22967 | 21433 | 4.87 | 95.11% | 95.25% | 0.21% | 102.18% | 101.78% | 0.56% |
| A2 | | | | 23624 | 22790 | 21498 | 4.9 | 95.40% | | | 101.38% | | |
| A2 | 16% | 99.45% | 105.35% | 104.10% | 101.78% | 95.25% | | | | | | | |
| A4 | 2133 | 15445 | 17702 | 18384 | 17896 | 18671 | 4.69 | 82.71% | 80.76% | 2.76% | 79.39% | 77.18% | 3.13% |
| A4 | | | | 17990 | 16914 | 17805 | 4.71 | 18.82% | | | 74.97% | | |
| A4 | 8% | 68.45% | 78.36% | 80.78% | 77.18% | 80.76% | | | | | | | |
| A7 | 1853 | 6549 | 9690 | 13269 | 12926 | 13780 | 4.85 | 60.69% | 59.99% | 0.99% | 57.02% | 58.20% | 1.68% |
| A7 | | | | 12934 | 13453 | 13469 | 4.79 | 59.29% | | | 59.39% | | |
| A7 | 7% | 28.40% | 42.30% | 57.88% | 58.20% | 59.99% | | | | | | | |
| A8 | 2419 | 18090 | 22093 | 22142 | 22070 | 22054 | 4.75 | 97.89% | 96.03% | 2.63% | 98.13% | 93.88% | 6.01% |
| A8 | | | | 20165 | 20181 | 21226 | 4.80 | 94.17% | | | 89.63% | | |
| A8 | 10% | 80.31% | 98.03% | 94.08% | 93.88% | 96.03% | | | | | | | |
| A10 | 1943 | 13660 | 20796 | 20834 | 21396 | 20110 | 4.83 | 89.20% | 91.02% | 2.58% | 95.13% | 94.82% | 0.16% |
| A10 | | | | 20773 | 21250 | 20921 | 4.82 | 92.85% | | | 94.49% | | |
| A10 | 8% | 60.42% | 92.30% | 92.56% | 94.82% | 91.02% | | | | | | | |
| A11 | 1611 | 10141 | 16955 | 18527 | 19642 | 18925 | 4.79 | 83.79% | 83.87% | 0.11% | 87.18% | 87.74% | 0.80% |
| A11 | | | | 19191 | 19893 | 18961 | 4.85 | 83.95% | | | 88.31% | | |
| A11 | 6% | 44.54% | 74.94% | 83.73% | 87.74% | 83.87% | | | | | | | |

TABLE 14

Enzymatic Hydrolysis of Xylan to Xylose by Ctec 3 cellulases (HPLC)

| Xylose (ppm) conversions | Time (h) | | | | | | Yield (%) | Yeild Avg | STDev |
|---|---|---|---|---|---|---|---|---|---|
| | 0 | 6 | 24 | 52 | 72 | 168 | | | |
| blank | 144 | 127 | 158 | 141 | 159 | 184 | 0.00 | | |
| SRP Control | 876 | 1841 | 2888 | 3563 | 3858 | 4139 | 151% | 151.00% | |
| SRP Control | 28% | 65% | 104% | 131% | 141% | 151% | | | |
| A2 | 960 | 1989 | 2327 | 2360 | 2348 | 2244 | 68% | 93% | 36% |
| A2 | | | | 2404 | 2327 | 2245 | 119% | | |
| A2 | 0.00% | 54.51% | 72.41% | 75.32% | 72.97% | 68.04% | | | |
| A4 | 718 | 2413 | 2964 | 3393 | 3371 | 3651 | 59% | 64% | 7% |
| A4 | | | | 3268 | 3137 | 3455 | 70% | | |
| A4 | 0.00% | 34.10% | 45.19% | 52.56% | 51.02% | 57.04% | | | |
| A7 | 271 | 485 | 585 | 929 | 893 | 1110 | 154% | 172% | 26% |
| A7 | | | | 917 | 957 | 1042 | 191% | | |
| A7 | 0.00% | 39.21% | 57.54% | 119.48% | 119.48% | 147.51% | | | |
| A8 | 771 | 1062 | 1324 | 1491 | 1504 | 1631 | 86% | 86% | 1% |
| A8 | | | | 1386 | 1411 | 1645 | 87% | | |
| A8 | 0.00% | 28.99% | 55.10% | 66.50% | 68.40% | 86.38% | | | |
| A10 | 784 | 1099 | 1564 | 1736 | 1814 | 1928 | 97% | 127% | 51% |
| A10 | | | | 1751 | 1814 | 2058 | 163% | | |
| A10 | 0.00% | 24.96% | 61.80% | 76.02% | 81.60% | 95.79% | | | |
| A11 | 814 | 1122 | 1620 | 1958 | 2122 | 2405 | 81% | 98% | 25% |
| A11 | | | | 1994 | 2102 | 2282 | 116% | | |
| A11 | 0.00% | 15.59% | 40.81% | 58.83% | 65.71% | 77.43% | | | |

TABLE 15

Solids loading and glucan to glucose enzymatic conversion

| | Time of digestion | Bagasse % conversion to glucose | Eucalyptus % conversion to glucose |
|---|---|---|---|
| 2% solids | 6 hrs | 99.45% | 80.31% |
| 10% solids | 6 hrs | 94% | 83% |
| 2% solids | 24 hrs | 98.08% | 105.35% |
| 10% solids | 18 hrs | 109% | 103% |

Bagasse Glycell treatment 2% solids (from table 13; A2)
*Eucalyptus* Glycell treatment 2% solids (from table 13; A8)
Bagasse Glycell treatment 10% solids
*Eucalyptus* Glycell treatment 10% solids Example 3

The objective of this trial was to evaluate alkali deacetylation prior to acid impregnation and digestion of *eucalyptus* chips with glycerol in an attempt to improve on those pretreatment methods for lignocellulosic material previously described.

Materials and Methods

Figure 3:
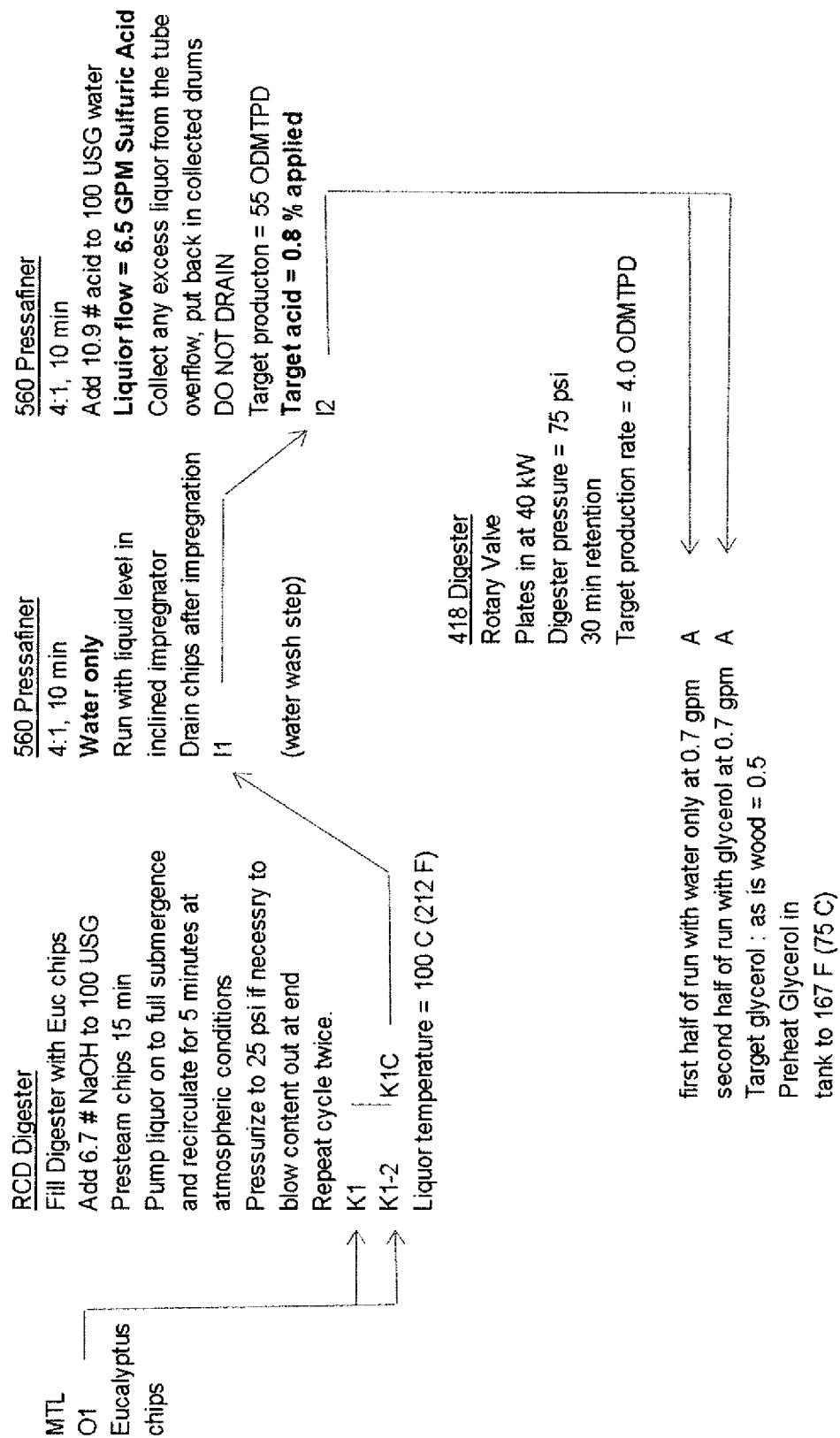
FIG. 3 outlines the pretreatment method of Example 3 including alkali deacetylation prior to acid impregnation and digestion of *eucalyptus* chips.

Trial runs involving deacetylation prior to acid impregnation were run in a similar manner to Example 2 but with a deacetylation pre-digestion step as per FIGS. 3 and 4. The deacetylation was conducted in a recirculating batch reactor with steam injection. Deacetylation is a stoichiometric reaction of a hydroxide and acetate groups covalently linked to hemicellulose component of the lignocellulosic material. Accordingly, the amount of hydroxide ion required was determined by titration in the following manner. *Eucalyptus* chips were ground to pass through a 2.83 mm (No. 7) screen. 20 g of the ground wood (as is at approximately 50% moisture) was placed in a beaker with approximately 250 ml of water and few drops of phenolphthalein. The mixture was stirred, heated to approximately 90° C. and titrated with 0.5% sodium hydroxide to end point over 90 minutes to assure complete deacetylation. The maximum dose of sodium hydroxide into the recirculating batch reactor was calculated from this titration. This in turn assured complete reaction of the hydroxide and minimised the amount of acid needed to achieve appropriate reaction conditions in step (i), the acid impregnation step.

Results

Figure 5:
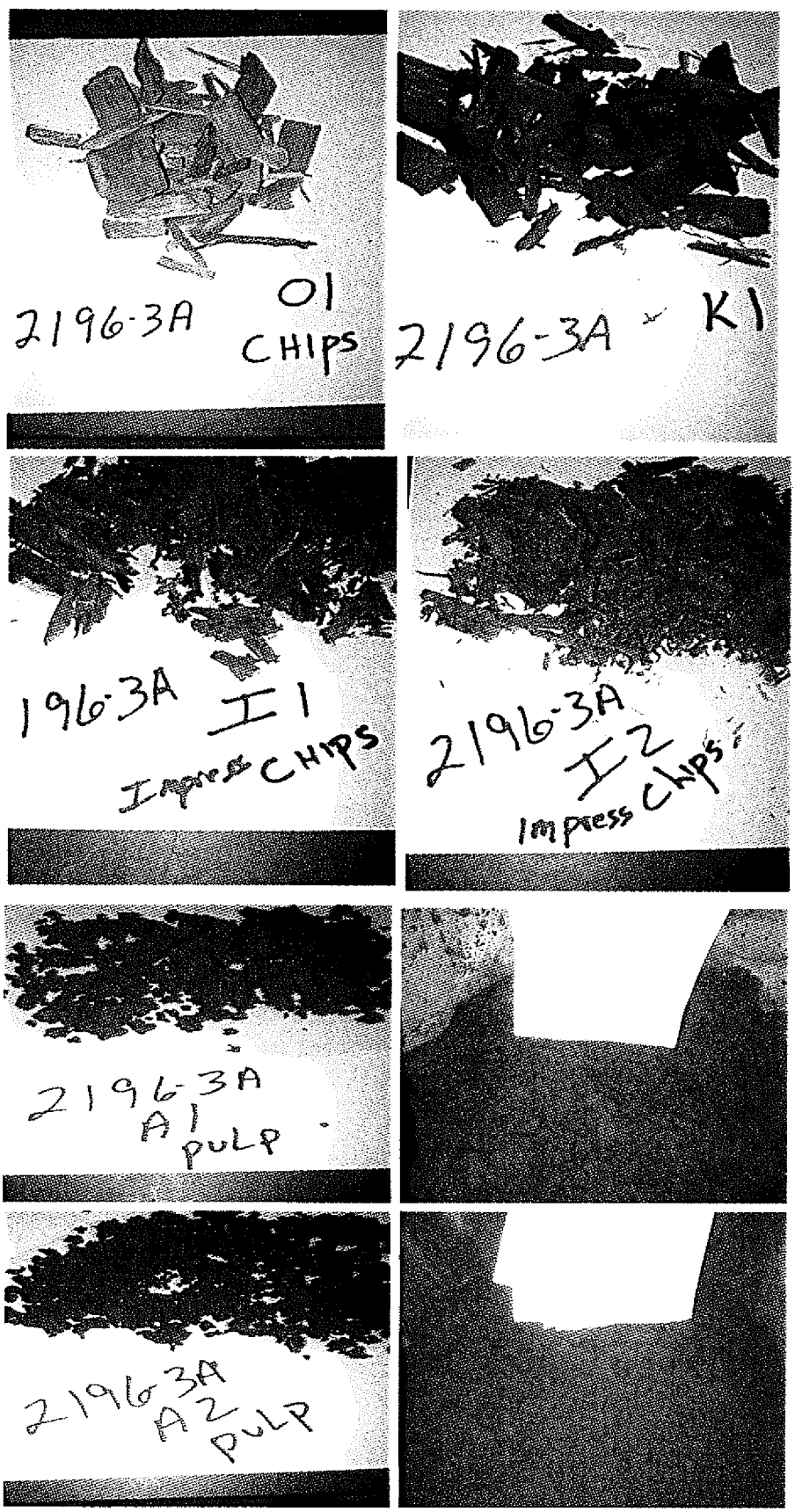
FIG. 5 provides images of the *eucalyptus* chips from Example 3 after various steps of the pretreatment method including alkali deacetylation.

As can be observed in FIG. 5, visually both A1 (water control) and A2 (with glycerol) were well reacted. The filtrate from the chips after 12 impregnation was approximately 1.4 pH. The A2 (with glycerol) sample was visually darker and seemingly more digested than the control A1 sample.

Example 4

The objective of this trial was to prepare a hexose rich sugars syrup from the partially hydrolysed lignocellulosic material produced from the treatment methods described herein, and in so doing demonstrate the enzyme catalysed saccharification or hydrolysis of the partially hydrolysed lignocellulosic material to sugars. A further objective of this trial was to subject the hexose rich sugars syrup to fermentation with four different microbes and in so doing demonstrate that the hexose rich sugars syrup is a suitable carbon source for microbial growth (i.e., that it does not contain inhibitors to growth that may be found in sugars syrups prepared from lignocellulosic materials by methods other than described herein).

Materials and Methods

Poplar wood chips were initially steamed by direct steam injection and then compressed, de-structured, and impregnated with sulfuric acid in an Andritz 560 GS Impressafiner prior to being fed into a 418 horizontal pressurized digester. Glycerol with was then added to the impregnated wood chips at the inlet to the digester. The initial chip destructuring and impregnation were performed on the wood substrates in an attempt to better penetrate their fibrous structure during the pretreatment process. After digestion in the 418 horizontal pressurized digester at 160° C. for 30 minutes the digested lignocellulosic material was collected in drums.

30 kg of digested lignocellulosic material was washed in 140 L of purified water to remove residual glycerol and solutes. The washed material was added to stainless steel mixing vessel MV-11 and suspended in purified water, pH was adjusted to 4.5 with 1M NaOH. Purified water was added to a final volume of 110 L. The suspension was pasteurised by heating to 71° C. then allowed to cool to 63° C. where it was held for 30 minutes. 12.5 L of a commercially available cellulose enzyme cocktail was added to the suspension and the reactor maintained at 50° C. with agitation. Glucose production was monitored over time.

After a period of time that the saccharification process was deemed complete, the mixture was filtered a fine mesh filter under 1.5 bar of pressure and the liquid component was further polished using a Pall Supradisc II depth filter, and then concentrated to a syrup of 67.6 g/100 g consistency.

Portions of this sugars syrup were diluted with water and media components as indicated in Table 16 below, and inoculated with cultures of *Pichia holisti, Saccharomyces cerevisiae* and *Escherichia coli*.

Results

Decreases in glucose concentration and corresponding increases in cell density shown in Tables 17 to 19 and FIG. 6 for each for the ferments demonstrates the glucose solution produced by the method described herein can be utilised as a carbon source.

TABLE 16

Fermentation Parameters

|  | Ferment 1 | — | Ferment 2 | — | Ferment 3 | — |
|---|---|---|---|---|---|---|
| Organism | *P. holstii* |  | *S. cerevisiae* |  | *E. coli* |  |
| Media (2 L) | Tryptone | 5 g/L | Tryptone | 5 g/L | Tryptone | 10 g/L |
| — | Yeast Extract | 6 g/L | Yeast Extract | 6 g/L | Yeast Extract | 5 g/L |
| — | MgSO4•7H2O | 1 g/L | MgSO4•7H2O | 1 g/L | NaCl | 10 g/L |
| — | KH2PO4 | 5 g/L | KH2PO4 | 5 g/L |  |  |
| — | Leaf Glucose Solution | 44 ml/L | Leaf Glucose Solution | 44 ml/L | Leaf Glucose Solution | 44 ml/L |
| — | Antifoam C | 1 ml/L | Antifoam C | 1 ml/L | Antifoam C | 1 ml/L |
| pH | 5.5 |  | 5.5 |  | 7.0 |  |
| Temperature | 30° C. |  | 30° C. |  | 37° C. |  |
| Agitation | 300 rpm |  | 300 rpm |  | 300 rpm |  |
| Air flow | 4 L/min |  | 4 L/min |  | 4 L/min |  |

TABLE 17

*Pichia holstii*

| Time (hours) | Glucose Conc. (g/L) | Optical Density (600 nm) |
|---|---|---|
| 0 | 17.25 | 0.002 |
| 3.7 | 15 | 0.646 |
| 6 | 14.13 | 0.724 |
| 10 | 12.87 | 0.873 |
| 21.5 | 0.5 | 17.6 |

TABLE 18

*Saccharomyces cerevisiae*

| Time (hours) | Glucose Conc. (g/L) | Optical Density (600 nm) |
|---|---|---|
| 0 | 16.24 | 4.4 |
| 2 | 14.64 | 5.5 |
| 4.35 | 8.16 | 6.58 |
| 6 | 1.16 | 9.56 |
| 8 | 0.54 | 13.2 |

TABLE 19

*Escherichia coli*

| Time (hours) | Glucose Conc. (g/L) | Optical Density (600 nm) |
|---|---|---|
| 0 | 16.28 | 0.115 |
| 2 | 14.44 | 2.6 |
| 4.35 | 4.92 | 8.5 |
| 6 | 0.92 | 11.5 |
| 8 | 0.49 | 13.36 |

Example 5

Glycell pretreated poplar chips prepared in the same manner as in Example 4 above were evaluated to observe the effect of increasing biomass solids loading and decreasing enzyme dose on enzymatic hydrolysis.

Materials and Methods

Two samples were compared:
Glycell Treatment Process (i.e., sequential acid and glycerol treatment) as per Example 4—1.15% acid on biomass db, 55% glycerol
Dilute acid only—1.07% acid on biomass db, no glycerol
Conditions of Enzymatic Hydrolysis:
15% solids, pH 5.5, CTEC 3 at 12 mg/g of cellulose (40% less enzyme by loading)

Results

The initial cellulose saccharification rate of the Glycell pretreated biomass was 3.0 times that of dilute acid pretreatment. Final yield of monosaccharides from the Glycell pretreated biomass was 166.6% that of dilute acid pretreatment. Accordingly, a high solids concentration of the lignocellulosic material partially hydrolysed by the method described herein may be successfully enzymatically hydrolysed by a significantly lower concentration of enzyme.

The invention claimed is:

1. A method for producing a partially hydrolysed lignocellulosic material comprising the steps:
   (i) treating a lignocellulosic material with an acid and/or an alkali at a temperature from about 40° C. to about 99° C., wherein there is no washing, draining and/or pressing of the lignocellulosic material after treatment with the acid and/or alkali prior to the commencement of step (ii);
   (ii) further treating the lignocellulosic material treated with the acid and/or alkali in step (i) at a temperature from about 160° C. to about 220° with an agent that comprises a polyol, wherein the polyol is present in an amount from about 30% to about 100% by weight of the agent, wherein the agent is present at an amount of about 25% to about 150% by weight of the lignocellulosic material, and wherein the agent further comprises no acid by weight of the agent;
   thereby producing a partially hydrolysed lignocellulosic material.

2. The method of claim 1, wherein at step (i) the lignocellulosic material is treated with: (a) acid alone; (b) alkali alone; (c) sequentially with acid and then alkali; or (d) sequentially with alkali and then acid.

3. The method of claim 1, wherein the acid is selected from the group consisting of sulphuric acid, hydrochloric acid, phosphoric acid, hydrofluoric acid, hydrobromic acid, nitric acid, acid metal salts and any combination thereof.

4. The method of claim 3, wherein the acid is sulphuric acid.

5. The method of claim 1, wherein the alkali is selected from the group consisting of sodium hydroxide, potassium hydroxide, ammonium hydroxide, alkali metal salts and any combination thereof.

6. The method of claim 5, wherein the alkali is sodium hydroxide.

7. The method of claim 1, wherein step (i) comprises impregnating the acid and/or alkali into and/or onto the lignocellulosic material.

8. The method of claim 1, wherein (i) the acid is present in an amount of about 0.1% to about 5% by weight of the lignocellulosic material; and/or (ii) the alkali is present in an amount of about 0.1% to about 15% by weight of the lignocellulosic material.

9. The method of claim 1, wherein the polyol is selected from the group consisting of glycerol, ethylene glycol and any combination thereof.

10. The method of claim 9, wherein the polyol is glycerol.

11. The method of claim 1, wherein step (i) is carried out at a temperature from about 50° C. to about 75° C.

12. The method of claim 1, wherein step (ii) is carried out at a temperature of about 160° C.

13. The method of claim 1, wherein step (i) is carried out for a period of time from about 5 minutes to about 30 minutes.

14. The method of claim 1, wherein step (ii) is carried out for a period of time from about 15 minutes to about 60 minutes.

15. The method of claim 14, wherein step (ii) is carried out for a period of time of about 30 minutes.

16. The method of claim 1, wherein the agent is present at an amount of about 100% to about 130% by weight of the lignocellulosic material.

17. The method of claim 1, wherein step (i) comprises treating a lignocellulosic material with an acid or an alkali.

18. A method for producing a partially hydrolysed lignocellulosic material comprising the steps:
   (i) treating a lignocellulosic material with an acid and/or an alkali at a temperature from about 40° C. to about 99° C. and is carried out for a period of time from about 5 minutes to about 30 minutes, wherein there is no washing, draining and/or pressing of the lignocellulosic material after treatment with the acid and/or alkali prior to the commencement of step (ii);
   (ii) further treating the lignocellulosic material treated with the acid and/or alkali in step (i) at a temperature from about 160° C. to about 220° C. and is carried out for a period of time from about 15 minutes to about 45 minutes with an agent that comprises a polyol, wherein the polyol is present in an amount from about 30% to about 100% by weight of the agent, wherein the agent is present at an amount of about 25% to about 150% by weight of the lignocellulosic material and wherein the agent further comprises no acid by weight of the agent;
   thereby producing a partially hydrolysed lignocellulosic material.

* * * * *